(12) United States Patent
Holland et al.

(10) Patent No.: US 12,319,649 B1
(45) Date of Patent: Jun. 3, 2025

(54) CANNABIDIOLIC ACID COCRYSTALS

(71) Applicant: Manoira Corporation, Tuxedo Park, NY (US)

(72) Inventors: Joanne Holland, Cambridge (GB); Alex Eberlin, Cambridge (GB)

(73) Assignee: Manoira Corporation, Tuxedo Park, NY (US)

( * ) Notice: Subject to any disclaimer, the term of this patent is extended or adjusted under 35 U.S.C. 154(b) by 0 days.

(21) Appl. No.: 18/790,366

(22) Filed: Jul. 31, 2024

Related U.S. Application Data

(62) Division of application No. 18/638,472, filed on Apr. 17, 2024.

(60) Provisional application No. 63/623,933, filed on Jan. 23, 2024.

(51) Int. Cl.
  *C07C 65/105* (2006.01)

(52) U.S. Cl.
  CPC ........ *C07C 65/105* (2013.01); *C07B 2200/13* (2013.01)

(58) Field of Classification Search
  CPC .................... C07C 65/105; C07B 2200/13562
  See application file for complete search history.

(56) References Cited

U.S. PATENT DOCUMENTS

2021/0213083 A1* 7/2021 Leuer .................. A61K 9/1694

FOREIGN PATENT DOCUMENTS

| WO | WO2019118360 A1 | 6/2019 |
| WO | WO2021046303 A1 | 3/2021 |
| WO | WO2021234449 A1 | 11/2021 |
| WO | WO2023225403 A2 | 11/2023 |

OTHER PUBLICATIONS

Guo et al. Acta Pharmaceutica Sinica B 2021;11(8):2537-2564.*
International Application No. PCT/US2024/025277, Filing Date Apr. 18, 2024, International Search Report, Mailing Date Nov. 15, 2024.

* cited by examiner

*Primary Examiner* — Ana Z Muresan
(74) *Attorney, Agent, or Firm* — Kramer Levin Naftalis & Frankel LLP

(57) ABSTRACT

The present invention relates to compositions comprising a cannabidolic acid cocrystal. In particular, the cannabidiolic acid cocrystals include a cannabidiolic acid L-phenylalanine cocrystal, a cannabidiolic acid vanillin cocrystal, a cannabidiolic acid betaine cocrystal, a cannabidiolic acid ethyl maltol cocrystal, a cannabidiolic acid L-proline cocrystal and a cannabidiolic acid D-proline cocrystal. The present invention also relates to compositions, particularly pharmaceutical compositions comprising a cannabidiolic acid cocrystal and a pharmaceutically acceptable carrier. The present invention further relates to methods to treat a disease, disorder or condition in a patient by administering to the patient a therapeutically effective amount of cannabidiolic acid cocrystal or a pharmaceutical composition comprising a therapeutically effective amount of cannabidiolic acid cocrystal.

8 Claims, 32 Drawing Sheets

CANNABIDIOLIC ACID COCRYSTALS

CROSS-REFERENCE TO RELATED APPLICATION

This application is a divisional of U.S. Ser. No. 18/638,472 filed Apr. 17, 2024, which claims priority to and benefit of U.S. Provisional Patent Application No. 63/623,933, filed on Jan. 23, 2024, the content of which is incorporated herein by reference in its entirety.

BACKGROUND

Cannabidiol (CBD) is one of the most abundant phytocannabinoids found in cannabis extract that has potential medicinal effects. In cannabis plants, CBD (FIG. 1A) is present in acidic form as cannabidiolic acid (CBDA; FIG. 1B). Methods to extract CBD from plants typically rely on heat to decarboxylate CBDA to CBD. However, since decarboxylation occurs with heat, light or even time, it is virtually impossible to extract pure CBDA that is not contaminated with CBD.

The lack of availability of CBDA has hampered the pharmacological exploration and exploitation of the potential medicinal benefits of CBDA. The limited research so far into CBDA's potential pharmacological properties has revealed that this cannabinoid has medicinal properties in its own right. For example, CBDA was shown to inhibit nausea and vomiting in a rat model with significantly greater potency than CBD via a 5-HT$_{1A}$ activation mechanism (D. Bolognini et al, *British Journal of Pharmacology*, 2012; 168 (6): 1456-1470). Studies have also shown the potential anti-cancer benefits of CBDA (S. Takeda, *Journal of Natural Medicines*, 2017; 71:286-291). CBDA's ability to selectively inhibit COX-2 activity (S. Takeda, Drug Metab. Dispos., 2008; 36 (9): 1917-1921) offers the potential to explore CBDA as an anti-inflammatory drug. Furthermore, CBDA, like CBD, has shown promise in the treatment of depressive disorders, potentially via the 5-HT$_{1A}$ pathway. It is likely that CBDA will show greater efficacy than CBD in treating depressive disorders due to CDBA's 100-fold higher affinity for 5-HT$_{1A}$ than CBD (D. Bolognini et al, *British Journal of Pharmacology*, 2012; 168 (6): 1456-1470). For example, CBDA was shown to be more effective than CBD in treating epilepsy (WO2017025712).

Despite the significant potential of CBDA for pharmaceutical applications, difficulties in extracting pure CBDA from cannabis plant combined with the chemical instability of CBDA suggests that contamination of CBDA with CBD is inevitable. While it is possible to produce CBDA synthetically, the inventors have found that synthetically produced CBDA is not crystalline, and crystallization of CBDA often results in the degradation of the CBDA (FIG. 2). There is, therefore, a need to develop new crystalline forms of CBDA that are stable to decarboxylation or degradation under typical storage conditions in order to fully explore the pharmaceutical potential of CBDA.

SUMMARY

The present invention provides cannabidiolic acid cocrystals. The cannabidiolic acid cocrystals may be used in the manufacture of a medicament for use in the treatment of the diseases, disorders and conditions. In one exemplary embodiment, the composition comprises a cannabidiolic acid cocrystal. In one aspect, the cannabidolic acid cocrystal is selected from the group comprising a cannabidiolic acid L-phenylalanine cocrystal, a cannabidiolic acid vanillin cocrystal, a cannabidiolic acid betaine cocrystal, a cannabidiolic acid ethyl maltol cocrystal, a cannabidiolic acid L-proline cocrystal and a cannabidiolic acid D-proline cocrystal. In another aspect, the cannabidiolic acid cocrystal is selected from the group comprising a 1:1 cannabidiolic acid L-phenylalanine cocrystal, a 1:1 cannabidiolic acid vanillin cocrystal, a 1:1 cannabidiolic acid betaine cocrystal, a 1:1 cannabidiolic acid ethyl maltol cocrystal, a 1:1 cannabidiolic acid L-proline cocrystal, and a 1:1 cannabidiolic acid D-proline cocrystal.

In one aspect, the 1:1 cannabidiolic acid L-phenylalanine cocrystal is characterized by a powder X-ray diffraction pattern having at least three peaks selected from 3.1, 6.4, 18.4, 19.8, and 23.7°2θ±0.2 °2θ; or a powder X-ray diffraction pattern substantially similar to FIG. 3; or an infrared spectrum having at least three peaks selected from 1606, 1409, 1296, 1240 and 1184 cm$^{-1}$±1 cm$^{-1}$; or an infrared spectrum substantially similar to FIG. 7.

In one aspect, the 1:1 cannabidiolic acid vanillin cocrystal is characterized by a powder X-ray diffraction pattern having at least three peaks selected from 4.3, 7.5, 14.2, 19.4, 22.2, and 25.2±0.2 °2θ; or a powder X-ray diffraction pattern substantially similar to FIG. 8; or an infrared spectrum having at least three peaks selected from 1658, 1509, 1294, 1258 and 1151 cm$^{-1}$±1 cm$^{-1}$; or an infrared spectrum substantially similar to FIG. 12.

In one aspect, the 1:1 cannabidiolic acid betaine cocrystal is characterized by a powder X-ray diffraction pattern having at least three peaks selected from 7.2, 11.0, 16.3, 18.4, and 23.6±0.2 °2θ; or a powder X-ray diffraction pattern substantially similar to FIG. 13; or an infrared spectrum having at least three peaks selected from 1723, 1589, 1371, 1261 and 887 cm$^{-1}$±1 cm$^{-1}$; or an infrared spectrum substantially similar to FIG. 17.

In one aspect, the 1:1 cannabidiolic acid ethyl maltol cocrystal is characterized by a powder X-ray diffraction pattern having at least three peaks selected from 8.4, 16.0, 17.1, 18.0, and 19.7±0.2 °2θ; or a powder X-ray diffraction pattern substantially similar to FIG. 18; or an infrared spectrum having at least three peaks selected from 1526, 1410, 1376, 1260 and 1238 cm$^{-1}$+1 cm$^{-1}$; or an infrared spectrum substantially similar to FIG. 22.

In one aspect, the 1:1 cannabidiolic acid L-proline cocrystal is characterized by a powder X-ray diffraction pattern having at least three peaks selected from 7.4, 8.5, 15.2, 19.0, and 23.0±0.2 °2θ; or a powder X-ray diffraction pattern substantially similar to FIG. 23; or an infrared spectrum having at least three peaks selected from 1574, 1430, 1374, 1240 and 1172 cm$^{-1}$+1 cm$^{-1}$; or an infrared spectrum substantially similar to FIG. 27.

In one aspect, the 1:1 cannabidiolic acid D-proline cocrystal is characterized by a powder X-ray diffraction pattern having at least three peaks selected from 4.8, 5.1, 9.1, 18.2, and 19.1±0.2 °2θ; or a powder X-ray diffraction pattern substantially similar to FIG. 28; or an Infrared Spectrum having at least three peaks selected from 1635, 1611, 1575, 1374 and 1244 cm$^{-1}$±1 cm$^{-1}$; or an infrared spectrum substantially similar to FIG. 32.

In another exemplary embodiment, the composition comprises a cannabidiolic acid cocrystal and an excipient. In one aspect, the cannabidiolic cocrystal is selected from the group comprising a cannabidiolic acid L-phenylalanine cocrystal, a cannabidiolic acid vanillin cocrystal, a cannabidiolic acid betaine cocrystal, a cannabidiolic acid ethyl maltol cocrystal, a cannabidiolic acid L-proline cocrystal and a cannabidiolic acid D-proline cocrystal. In another aspect, the cannabidiolic cocrystal is selected from the group comprising a 1:1 cannabidiolic acid L-phenylalanine cocrystal, a 1:1 cannabidiolic acid vanillin cocrystal, a 1:1 cannabidiolic acid betaine cocrystal, a 1:1 cannabidiolic acid ethyl maltol cocrystal, a 1:1 cannabidiolic acid L-proline cocrystal and a 1:1 cannabidiolic acid D-proline cocrystal.

In another exemplary embodiment, the pharmaceutical composition comprises a cannabidiolic acid cocrystal and a pharmaceutically acceptable carrier. In one aspect, the cannabidiolic cocrystal is selected from the group comprising a cannabidiolic acid L-phenylalanine cocrystal, a cannabidiolic acid vanillin cocrystal, a cannabidiolic acid betaine cocrystal, a cannabidiolic acid ethyl maltol cocrystal, a cannabidiolic acid L-proline cocrystal and a cannabidiolic acid D-proline cocrystal. In another aspect, the cannabidiolic cocrystal is selected from the group comprising a 1:1 cannabidiolic acid L-phenylalanine cocrystal, a 1:1 cannabidiolic acid vanillin cocrystal, a 1:1 cannabidiolic acid betaine cocrystal, a 1:1 cannabidiolic acid ethyl maltol cocrystal, a 1:1 cannabidiolic acid L-proline cocrystal and a 1:1 cannabidiolic acid D-proline cocrystal.

In one aspect, the pharmaceutical composition comprises a therapeutically effective amount of a cannabidiolic acid cocrystal. In a further aspect, the therapeutically effective amount of the cannabidiolic acid cocrystal is about 0.01 mg/kg, about 0.02 mg/kg, about 0.05 mg/kg, about 0.1 mg/kg, about 0.2 mg/kg, about 0.5 mg/kg, about 1 mg/kg, about 2 mg/kg, about 5 mg/kg, about 10 mg/kg, about 20 mg/kg, about 50 mg/kg, about 100 mg/kg, about 200 mg/kg, about 500 mg/kg, about 50 mg, about 100 mg, about 250 mg, about 500 mg, about 750 mg, about 1,000 mg, about 1,500 mg, about 2,000 mg, about 50 mg to about 1500 mg, about 100 mg to about 1000 mg, or about 250 mg to about 750 mg.

In another exemplary embodiment, a method of treating a disease, disorder or condition of a patient comprises administering to the patient a therapeutically effective amount of a cannabidiolic acid cocrystal or a pharmaceutical composition comprising a a therapeutically effective amount of a cannabidiolic acid cocrystal and a pharmaceutically acceptable carrier. In one aspect, the cannabidiolic acid cocrystal is selected from the group comprising: a cannabidiolic acid L-phenylalanine cocrystal, a cannabidiolic acid vanillin cocrystal, a cannabidiolic acid betaine cocrystal, a cannabidiolic acid ethyl maltol cocrystal, a cannabidiolic acid L-proline cocrystal, and a cannabidiolic acid D-proline cocrystal. In another aspect, the cannabidiolic cocrystal is selected from the group comprising a 1:1 cannabidiolic acid L-phenylalanine cocrystal, a 1:1 cannabidiolic acid vanillin cocrystal, a 1:1 cannabidiolic acid betaine cocrystal, a 1:1 cannabidiolic acid ethyl maltol cocrystal, a 1:1 cannabidiolic acid L-proline cocrystal and a 1:1 cannabidiolic acid D-proline cocrystal.

In one aspect, the patient is an animal. In one aspect, the patient is a human.

In one aspect, the therapeutically effective amount of the cannabidiolic acid cocrystal is about 0.01 mg/kg, about 0.02 mg/kg, about 0.05 mg/kg, about 0.1 mg/kg, about 0.2 mg/kg, about 0.5 mg/kg, about 1 mg/kg, about 2 mg/kg, about 5 mg/kg, about 10 mg/kg, about 20 mg/kg, about 50 mg/kg, about 100 mg/kg, about 200 mg/kg, about 500 mg/kg, about 50 mg, about 100 mg, about 250 mg, about 500 mg, about 750 mg, about 1,000 mg, about 1,500 mg, about 2,000 mg, about 50 mg to about 1500 mg, about 100 mg to about 1000 mg, or about 250 mg to about 750 mg.

In one aspect, the cannabidiolic cocrystal is administered to the patient as a solid, a semi-solid, a lyophilized powder, or a liquid dosage form.

In another exemplary embodiment, a method of preparing a liquid pharmaceutical composition comprises the step of dissolving a cannabidiolic acid cocrystal in a pharmaceutically acceptable solvent.

In one aspect, the cannabidiolic cocrystal is selected from the group comprising a cannabidiolic acid L-phenylalanine cocrystal, a cannabidiolic acid vanillin cocrystal, a cannabidiolic acid betaine cocrystal, a cannabidiolic acid ethyl maltol cocrystal, a cannabidiolic acid L-proline cocrystal, and a cannabidiolic acid D-proline cocrystal. In another aspect, the cannabidiolic cocrystal is selected from the group comprising: a 1:1 cannabidiolic acid L-phenylalanine cocrystal, a 1:1 cannabidiolic acid vanillin cocrystal, a 1:1 cannabidiolic acid betaine cocrystal, a 1:1 cannabidiolic acid ethyl maltol cocrystal, a 1:1 cannabidiolic acid L-proline cocrystal, and a 1:1 cannabidiolic acid D-proline cocrystal.

DETAILED DESCRIPTION

Recent years have seen a significant escalation in scientific research into the potential medicinal benefits of the phytocannabinoid, cannabidiol (CBD). This has led to FDA approval for the treatment of rare forms of epilepsy, as well as a rapidly growing market for consumer products containing CBD. While CBD is one of the most abundant phytocannabinoids found in cannabis extract, CBD often exists in acidic form, cannabidiolic acid (CBDA), within the plant. Methods to extract CBD from plants typically rely on heat to decarboxylate the carboxylic acid form into CBD. More recent methods of extraction using $CO_2$ have allowed for retention of a percentage of CBDA. However, since decarboxylation occurs with heat, light or even time, it is virtually impossible to extract pure CBDA that is not contaminated with CBD.

The lack of availability of CBDA has hampered the pharmacological exploration and exploitation of the potential medicinal benefits of CBDA. The limited research so far into CBDA's potential pharmacological properties has revealed that this cannabinoid has medicinal properties in its own right. For example, CBDA was shown to inhibit nausea and vomiting in a rat model with significantly greater potency than CBD via a $5-HT_{1A}$ activation mechanism (D. Bolognini et al, *British Journal of Pharmacology*, 2012; 168 (6): 1456-1470). Studies have also shown the potential anti-cancer benefits of CBDA (S. Takeda, *Journal of Natural Medicines*, 2017; 71:286-291). CBDA's ability to selectively inhibit COX-2 activity (S. Takeda, Drug Metab. Dispos., 2008; 36 (9): 1917-1921) offers the potential to explore CBDA as an anti-inflammatory drug. Furthermore, CBDA, like CBD, has shown promise in the treatment of depressive disorders, potentially via the $5-HT_{1A}$ pathway. It is likely that CBDA will show greater efficacy than CBD in treating depressive disorders due to CBDA's 100-fold higher affinity for $5-HT_{1A}$ than CBD (D. Bolognini et al, *British Journal of Pharmacology*, 2012; 168 (6): 1456-1470). For example, CBDA was shown to be more effective than CBD in treating epilepsy (WO2017025712).

Figure 1A:
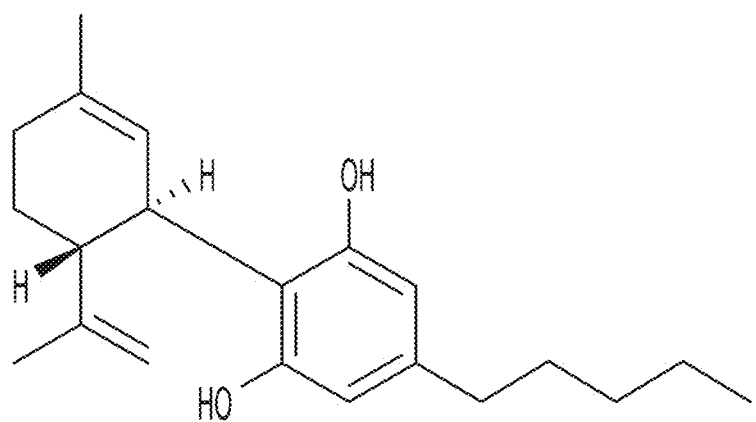
FIG. 1A depicts the structure of cannabidiol.
Figure 1B:
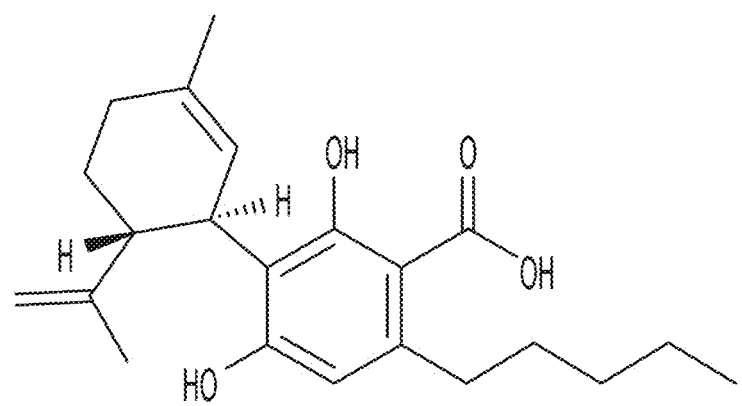
FIG. 1B depicts the structure of cannabidiolic acid.
Figure 2:
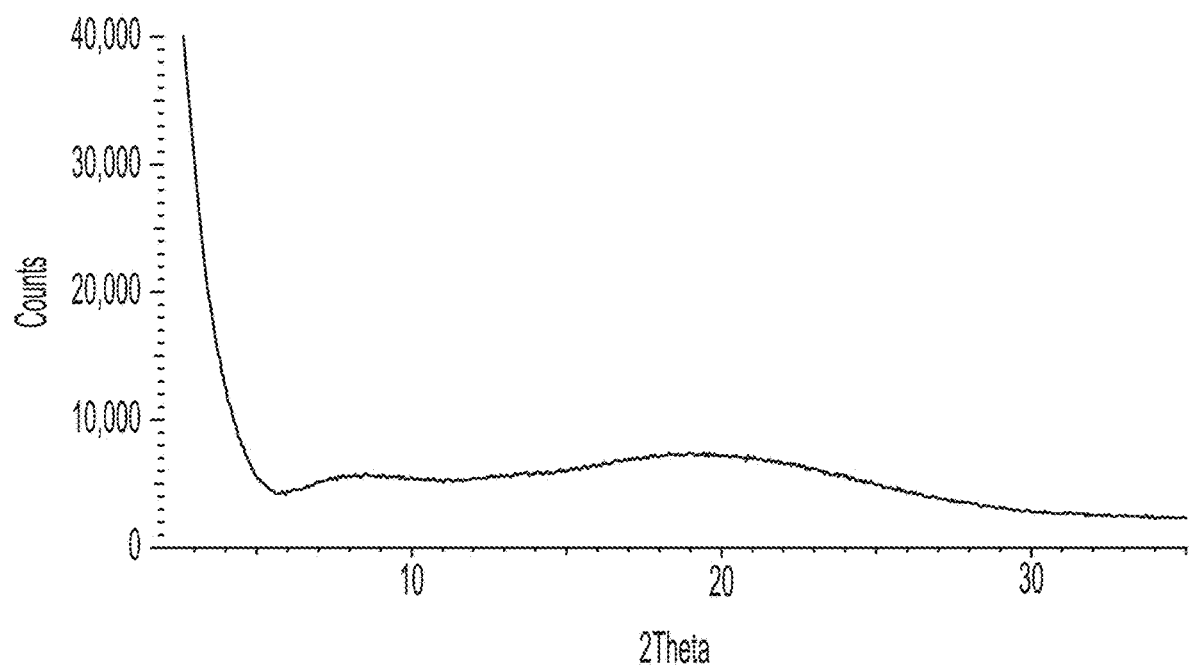
FIG. 2 depicts the X-ray powder diffraction (XRPD) diagram for synthetic cannabidiolic acid.

Despite the significant potential CBDA may possess for pharmaceutical applications, difficulties in extracting pure CBDA from cannabis plant combined with the chemical instability of CBDA suggests that contamination of CBDA with CBD is inevitable. While it is possible to produce CBDA synthetically, the inventors have found that synthetically produced CBDA is not crystalline and crystallization of CBDA often results in the degradation of the CBDA (FIG. 2). There is, therefore, a need to develop new crystalline forms of CBDA that are stable to decarboxylation or degradation under typical storage conditions in order to fully explore the pharmaceutical potential of CBDA.

The chemical composition and solid-state form (e.g., the crystalline or amorphous form) of an active pharmaceutical ingredient (API) can be critical to its pharmacological properties, such as bioavailability, and to its development as a viable drug candidate. Each composition or crystalline form can have different solid state (physical and chemical) properties. The differences in physical properties exhibited by a novel solid-state form (such as, for example, a polymorph of the API or a cocrystal containing the API, discussed below) may affect pharmaceutical and pharmacological properties such as storage, stability, compressibility and density (important factors in formulation and product manufacturing), and/or solubility and dissolution rates (important factors in determining bioavailability). For example, the rate of dissolution of an active ingredient in a patient's stomach fluid may have therapeutic consequences since it impacts the rate at which an orally administered active ingredient may reach the patient's bloodstream.

Physical properties of an API can also have a major influence on the ability to deliver a drug by a desired method. For example, if a medication is administered by inhalation, physical properties relating to the API as a particle, such as morphology, density, surface energy, charge, hygroscopicity, stability, dispersive properties and/or agglomeration, may be relevant. The solid-state form of the API, and as described below, cocrystals of the API, provide opportunities to address, engineer, and/or improve upon one or more of such properties and thereby upon methods of delivery.

Obtaining crystalline forms of an API, when possible, is extremely useful in drug development. It permits better characterization of the drug candidate's chemical and physical properties, and can reduce the time and cost of drug development. Crystalline forms often have better chemical and physical properties than the API in its amorphous state.

It may be possible to achieve more desirable properties of a particular API by forming a cocrystal of the API. A cocrystal of an API is a distinct chemical composition of the API and coformer(s), and generally possesses distinct crystallographic and spectroscopic properties when compared to those of the API and coformer(s) individually. Crystallographic and spectroscopic properties of crystalline forms are typically measured by X-ray powder diffraction (XRPD) and single crystal X-ray crystallography, among other techniques. Cocrystals often also exhibit distinct thermal behavior, which can be measured by techniques such as capillary melting point, thermogravimetric analysis (TGA), and differential scanning calorimetry (DSC). Cocrystals can also possess more favorable solid state, physical, chemical, pharmaceutical, and/or pharmacological properties, and can be easier to process than known forms or formulations of an API. For example, a cocrystal may have different dissolution and/or solubility properties than the API and can therefore be more effective in therapeutic delivery. Formation of a cocrystal can also be used to avoid polymorph formation of the drug. Therefore, new pharmaceutical compositions comprising a cocrystal of a given API may have different or superior properties as compared to its existing drug formulations.

Unlike salts, which possess a neutral net charge but comprise charge-balanced components, cocrystals are comprised of neutral species. Thus, unlike a salt, one cannot determine the stoichiometry of a cocrystal based on charge balance. Indeed, cocrystals can have stoichiometric ratios of drug to coformer of greater than or less than 1:1. The stoichiometric ratio of an API to coformer is a generally an unpredictable feature of a cocrystal.

The present invention discloses compositions comprising a cannabidiolic acid cocrystal, compositions comprising a cannabidiolic acid and one or more excipients, and in particular pharmaceutical compositions comprising a cannabidiolic acid cocrystal and a pharmaceutically acceptable carrier. The invention also discloses methods of treatment for the diseases, disorders and conditions with a therapeutically effective amount of a cannabidiolic acid cocrystal, or a pharmaceutical composition comprising the cocrystal, for that treatment. The invention further provides use of a cannabidiolic acid cocrystal in the manufacture of a medicament for use in the treatment of diseases, disorders and conditions described herein.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described.

The term "a" should be understood to mean "at least one" and the terms "about" and "approximately" should be understood to permit standard variation as would be understood by those of ordinary skill in the art, and where ranges are provided, endpoints are included. As used herein, the terms "include," "includes," and "including" are meant to be non-limiting and are understood to mean "comprise," "comprises," and "comprising" respectively.

In some exemplary embodiment, the disclosure provides a composition comprising a cannabidiolic acid cocrystal.

As used herein, the term "cocrystal" refers to a multi-component crystal composed of two or more neutral molecules at a stoichiometric ratio and bonded together via non-covalent interactions (e.g., hydrogen bonds, van der Waal forces). In certain exemplary embodiments, the components of the cocrystal can include an active pharmaceutical ingredient (API) and a coformer.

The term "an active pharmaceutical ingredient" or "API" refers to the biologically active component of a drug product. An active pharmaceutical agent can refer to any substance or combination of substances used in a drug product, intended to furnish pharmacological activity or to otherwise have direct effect in the diagnosis, cure, mitigation, treatment or prevention of disease, or to have direct effect in restoring, correcting or modifying physiological functions in animals. Non-limiting methods to prepare an active pharmaceutical agent can include using fermentation process, recombinant DNA, isolation and recovery from natural resources, chemical synthesis, or combinations thereof.

In some exemplary embodiments, the cannabidiolic acid active pharmaceutical ingredient is formulated as a cannabidiolic acid cocrystal. In some exemplary embodiments, the cannabidiolic acid cocrystals can include, but are not limited to, a cannabidiolic acid L-phenylalanine cocrystal, a cannabidiolic acid vanillin cocrystal, a cannabidiolic acid betaine cocrystal, a cannabidiolic acid ethyl maltol cocrystal, a cannabidiolic acid L-proline cocrystal and a cannabidiolic acid D-proline cocrystal. In some exemplary embodiments, the cannabidiolic acid cocrystals can include, but are not limited to, a 1:1 cannabidiolic acid L-phenylalanine cocrystal, a 1:1 cannabidiolic acid vanillin cocrystal, a 1:1 cannabidiolic acid betaine cocrystal, a 1:1 cannabidiolic acid ethyl maltol cocrystal, a 1:1 cannabidiolic acid L-proline cocrystal and a 1:1 cannabidiolic acid D-proline cocrystal. These cannabidiolic acid cocrystals, their preparation, and their characterization are described in the examples and figures herein.

The term "coformer" refers to a co-crystallizing agent that interacts via non-covalent interactions with the API in the crystal lattice. The coformer is not required to have an activity of its own, although it may have some activity. Some coformers may facilitate the therapeutic effect of an API. For pharmaceutical formulations, the coformer may be a pharmaceutically acceptable molecule that forms a cocrystal with the API or its salt. The coformer may be non-ionized, such as, for example, benzoic acid, succinic acid, and caffeine, or zwitterionic, such as, for example, L-lysine, L-arginine, or L-proline, or may be a salt, such as, for example, sodium benzoate or sodium succinate. Coformers may also include, but are not limited to, organic bases, organic salts, alcohols, aldehydes, amino acids, sugars, ionic inorganics, carboxylic acids, amines, flavoring agents, sweeteners, nutraceuticals, aliphatic esters, aliphatic ketones, organic acids, aromatic esters, alkaloids, and aromatic ketones.

The properties of the components or their salts, such as APIs or salts thereof, may be modified by forming a cocrystal. The cocrystal may have improved properties compared to the API itself or as a salt. Such properties include, for example, melting point, solubility, dissolution, chemical stability, physical stability, and bioavailability.

In some exemplary embodiments, the cannabidiolic acid cocrystals can be characterized by a powder X-ray diffraction pattern or an infrared spectrum having certain peaks or signals, or a powder X-ray diffraction pattern or an infrared spectrum that is substantially similar to a figure disclosed herein.

As used herein, the term "powder X-ray diffraction pattern" refers to a plot of measured signal intensity of X-rays for various angles of diffraction. For an amorphous material, an X-ray powder diffraction pattern may include one or more broad signals or peaks, whereas for a crystalline material, an X-ray powder diffraction pattern may include one or more sharp signals or peaks.

As used herein, the term "infrared spectrum" refers to a plot of measured signal intensity of infrared absorbance (or transmittance) versus frequency or wavelength of light.

As used herein, the term "peaks" or "signals" refer to relative signal intensities within a given powder X-ray diffraction pattern or an infrared spectrum.

As used herein, a powder X-ray diffraction pattern or an infrared spectrum is "substantially similar to [a particular] Figure" when at least 90%, or at least 95%, at least 98%, or at least 99%, of the signals in two powder X-ray diffraction patterns or two infrared spectra overlap. In determining "substantial similarity," a person skilled in the art will understand that there may be variation in the intensities and/or signal positions in the powder X-ray diffraction pattern or the infrared spectrum.

Therapeutic Uses of Cannabidiolic Acid Cocrystals

Cannabidiolic acid can have antiemetic, anticonvulsant, anti-inflammatory, antidepressant, and anti-cancer properties, and is known in the art to be useful in the treatment of various diseases, disorders and conditions. The cannabidiolic acid cocrystals of the present invention and pharmaceutical compositions containing the cannabidiolic acid cocrystals may then also be used to treat such diseases, disorders, and conditions.

Examples of such diseases, disorders, and conditions include, but are not limited to, anxiety and stress, depression, schizophrenia, panic and anxiety, withdrawal symptoms in cannabis and tobacco addiction, reward-facilitating effect of morphine and cocaine, auto-immune diseases of any type (diabetes type 1, GVHD being specific non-limiting examples), inflammation (Crohn's disease, colitis, pancreatitis, rheumatoid arthritis), reduction of infarct size and increase blood flow in stroke, obesity, metabolic syndrome, retinopathy associated with diabetes, nausea, myocardial, liver, renal ischemic/reperfusion injury, neuronal damage (due to neurological diseases or injury, Parkinson's disease, Huntington's disease, Alzheimer's disease, cerebral infarction, hepatic encephalopathy, pain, traumatic brain injury, cerebral ischemia, spinal cord injury, memory rescuing effects, cancer and resistance to cancer chemotherapy, cancer cell migration (metastasis), angiogenesis, epilepsy and convulsions, chronic inflammatory and neuropathic pain, airway obstruction, obsessive-compulsive behavior and any combinations thereof.

In another exemplary embodiment, the present invention discloses methods of treating such a disease, disorder, or condition in a patient comprising the step of administering to the patient a therapeutically effective amount of a cannabidiolic acid cocrystal or of administering to the patient a pharmaceutical composition comprising a cannabidiolic acid cocrystal.

As used herein, the term "patient" refers to any organism to which a pharmaceutical composition may be administered, e.g., for experimental, diagnostic, prophylactic, cosmetic, and/or therapeutic purposes. Typical patients include animals (e.g., mammals, such as mice, rats, rabbits, domestic animals such as dogs and cats, cows, sheep, pigs, horses, non-human primates, and/or humans). In some embodiments, the patient is suffering from or susceptible to one or more diseases, disorders, or conditions. In some embodiments, the patient has been diagnosed with one or more diseases, disorders, or conditions.

As used herein, the term "treatment" or "treating" means any treatment of a disease, disorder or condition in a mammal, including preventing or protecting against the disease, disorder or condition, that is, causing the clinical symptoms not to develop; inhibiting the disease, disorder or condition, that is, arresting or suppressing the development of clinical symptoms; and/or relieving the disease, disorder or condition (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the disease, disorder or condition. The term "protection" is meant to include "prophylaxis."

As used herein, the term "administering" refers to the administration of a compound, composition, dosage form and the like to a patient, subject or system. Administration to a patient may be facilitated by any appropriate route. For example, in some embodiments, administration may be bronchial, buccal, enteral, intradermal, intra-arterial, intragastric, intramedullary, intramuscular, intranasal, intraperitoneal, intrathecal, intravenous, intraventricular, mucosal, nasal, oral, rectal, subcutaneous, sublingual, topical, tracheal, transdermal, vaginal, and/or intravitreal. In some embodiments, administration may involve intermittent dosing. In some embodiments, administration may involve continuous dosing for at least a selected period of time.

Another aspect of the invention relates to the use of a cannabidiolic acid cocrystal of the invention in the treatment of diseases, disorders and conditions discussed above. Accordingly, the invention further relates to the manufacture of a medicament for use in the treatment of such diseases, disorders and conditions.

Pharmaceutical Compositions Containing Cannabidiolic Acid Cocrystals

In another exemplary embodiment, the present invention discloses pharmaceutical compositions comprising a cannabidiolic acid cocrystal and a pharmaceutically acceptable carrier. As mentioned above, these pharmaceutical compositions are therapeutically useful to treat or prevent disorders such as those discussed above.

As used herein, the term "pharmaceutical composition" refers to an active pharmaceutical ingredient (API) that is formulated with one or more pharmaceutically acceptable carrier.

As used herein, the term "carrier" refers to an agent that may be added to a formulation to provide a desired consistency, to improve stability, and/or adjust osmolality. Examples of commonly used carriers include, but are not limited to, sugars, polyols, amino acids, surfactants, and/or polymers. The terms "carrier" and "excipient" have the same meaning and are used interchangeably.

As used herein, the term "a therapeutically effective amount" refers to an amount that is sufficient, either by itself or in combination with one or more therapeutic agent, to partially or completely reduce the incidence of one or more symptoms, features, and/or causes of a particular disease, disorder, and/or condition, or to partially or completely prevent any of the aforesaid from worsening. A therapeutically effective amount may be, for example, about 0.01 mg/kg, about 0.02 mg/kg, about 0.05 mg/kg, about 0.1 mg/kg, about 0.2 mg/kg, about 0.5 mg/kg, about 1 mg/kg, about 2 mg/kg, about 5 mg/kg, about 10 mg/kg, about 20 mg/kg, about 50 mg/kg, about 100 mg/kg, about 200 mg/kg, or about 500 mg/kg. A therapeutically effective amount may also be, for example, about 50 mg, about 100 mg, about 250 mg, about 500 mg, about 750 mg, about 1,000 mg, about 1,500 mg, about 2,000 mg, about 50 mg to about 1500 mg, about 100 mg to about 1000 mg, or about 250 mg to about 750 mg. The actual amount required for treatment of any particular disease, disorder or condition for any particular patient may depend upon a variety of factors including, for example, the particular disease, disorder or condition being treated; the disease state being treated and its severity; the specific pharmaceutical composition employed; the age, body weight, general health, sex and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173, 2001, which is incorporated herein by reference.

The pharmaceutical composition of the invention may be in any pharmaceutical form which contains a cannabidiolic acid cocrystal. In some exemplary embodiments, the pharmaceutical composition may be formulated as a solid, a semi-solid, a lyophilized powder, or a liquid dosage form. The pharmaceutical composition may also be, for example, a tablet, a capsule, an oral solution, an injectable composition, a topical composition, an inhalable composition or a transdermal composition. Liquid pharmaceutical compositions may be prepared using a cannabidiolic acid cocrystal of the invention and represent a particular embodiment of the invention. For a liquid pharmaceutical composition, the cannabidiolic acid cocrystal may be dissolved in a solvent, e.g., water, at the time and point of care.

The term "dosage" refers to a physically discrete unit of one or more active pharmaceutical ingredients for administration to a patient. Each dosage contains a predetermined quantity of one or more active pharmaceutical ingredients. The term "dosage form" refers to the physical form in which the drug is manufactured or administered.

The pharmaceutical composition may also be formulated as a chewable lozenge, also known as a gummy-type lozenge. As is known in the art, chewable lozenge formulations may be prepared from glycerin, gelatin, and water. The lozenges typically also contain a flavorant such as a fruit or candy flavor, and a colorant to give the formulation a pleasant flavor and appearance. Chewable lozenges may also be made or molded into a variety of shapes such as, but not limited to, ovoid, spherical, platonic solids (e.g. tetrahedrons, cubes, octahedrons, etc.), rectangular prisms, cones, pyramids, cylinders, fruit slices, animals, cartoon characters, cars, etc. An exemplary chewable lozenge of the invention may contain a desired amount of the cocrystal, glycerin, gelatin, water, methylparaben, flavoring oil, and a colorant.

The pharmaceutical composition may also be formulated as a sublingual or buccal preparation—a tablet form not used as often as oral tablets. These small, hard compressed tablets are designed to dissolve rapidly in the vascular mucous membrane of the mouth. Buccal tablets are placed in the buccal pouch (between the check and the gum) and sublingual tablets are placed under the tongue. Because the buccal and sublingual areas are highly vascularized, drugs are quickly absorbed into the bloodstream with rapid onset of the drug effects. Drugs administered in this way avoid first-pass metabolism because the adsorbed drug bypasses the portal vein unlike drugs adsorbed from the gastrointestinal (GI) tract. Sublingual and buccal formulations may be prepared using pharmaceutically acceptable carriers and disintegrants known in the art as well as flavorants and other additives to improve taste and patient acceptance and compliance.

Inhalable compositions may be used to administer the pharmaceutical composition topically to the lung or within the nasal passages. An inhalable composition can include a dry powder inhaler formulation of respirable particles comprised of a cannabidiolic acid cocrystal, which the patient being treated inhales. It is common for a dry powder formulation to include carrier particles, to which the cocrystal particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose. The cocrystal would be dispersed into the respiratory tract in a therapeutically effective amount.

The pharmaceutical compositions can contain, for example, about 0.1% to about 99.9% by weight of a cannabidiolic acid cocrystal of the invention, for example, about 0.5% to about 99% by weight of a cannabidiolic acid cocrystal of the invention and, for example, 99.5% to 0.5% by weight of at least one suitable pharmaceutical excipient or solvent. In one embodiment, the composition may be between about 5% and about 75% by weight of a cannabidiolic acid cocrystal of the invention with the rest being at least one suitable excipient, solvent or at least one other adjuvant, as discussed below.

Depending on the type of composition, the excipient or pharmaceutically acceptable carrier may be chosen from any one or a combination of excipients or carriers known in the art. The choice of pharmaceutically acceptable carrier depends upon the pharmaceutical form and the desired method of administration to be used. For a pharmaceutical composition of the invention, that is one containing a cannabidiolic acid cocrystal, a carrier should be chosen that maintains the crystalline form. In other words, the carrier should not substantially alter the cannabidiolic acid cocrystal. Nor should the carrier be otherwise incompatible with a cannabidiolic acid cocrystal used, such as by producing any undesirable biological effect or otherwise interacting in a deleterious manner with any other component(s) of the pharmaceutical composition.

The pharmaceutical composition may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, a cannabidiolic acid cocrystal of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the art may also be used in the compositions and pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, the pharmaceutical composition may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing a cannabidiolic acid cocrystal of the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Compositions of the present invention may be intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

In addition to the topical method of administration described above, there are various methods of administering the active a cannabidiolic acid cocrystal of the present invention topically to the lung. One such means could involve a dry powder inhaler formulation of respirable particles comprised of a cannabidiolic acid cocrystal of the present invention, which the patient being treated inhales. It is common for a dry powder formulation to include carrier particle to which cannabidiolic acid cocrystal particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose.

In addition to the topical method of administration described above, there are various methods of administering the active cannabidiolic acid cocrystal systemically by such methods. One such means would involve an aerosol suspension of respirable particles comprised of a cannabidiolic acid cocrystal of the invention, which the patient being treated inhales. A cannabidiolic acid cocrystal would be absorbed into the bloodstream via the lungs in a pharmaceutically effective amount. The respirable particles can be liquid or solid, with a particle size sufficiently small to pass through the mouth and larynx upon inhalation.

Because the crystalline form of a cannabidiolic acid cocrystal may be maintained during preparation, solid dosage forms are one embodiment of the pharmaceutical composition of the invention. Dosage forms for oral administration, which includes capsules, tablets, pills, powders, granules, and suspensions may be used. Dosage forms for pulmonary administration, which includes metered dose inhaler, dry powder inhaler or aerosol formulations may be used. In such solid dosage forms, the active compound may be mixed with at least one inert, pharmaceutically acceptable excipient (also known as a pharmaceutically acceptable carrier).

The cannabidiolic acid cocrystal may also be used to formulate liquid or injectable pharmaceutical compositions. Administration of a cannabidiolic acid cocrystal in pure form or in an appropriate pharmaceutical composition may be carried out via any of the accepted modes of administration or agents for serving similar utilities. Thus, administration may be, for example, orally, buccally, nasally, pulmonary, parenterally (intravenous, intramuscular, or subcutaneous), topically, transdermally, intravaginally, intravesically, intrasystemically, ophthalmically or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

In another exemplary embodiment, the present invention discloses a method of preparing a liquid pharmaceutical composition comprising the step of dissolving a cannabidiolic acid cocrystal in a pharmaceutically acceptable solvent. As discussed above, liquid pharmaceutical compositions of the invention may be administered orally, parenterally (including by inhalation), and intravenously.

The present invention will be more fully understood by reference to the following Examples. They should not, however, be construed as limiting the scope of the invention.

EXAMPLES

The following analytical methods were used to characterize the cannabidiolic acid cocrystals of the invention:

X-Ray Powder Diffraction Characterization: X-ray powder diffraction patterns for the samples were acquired on a Bruker 2nd Gen D2-Phaser diffractometer using CuKα radiation (30V, 10 mA), θ-2θ goniometer, V4 receiving slits, a Ge monochromator and a Lynxeye detector. The instrument is performance checked using a certified Corundum standard (NIST 1976). The data were collected at ambient temperature over an angular range of 2° to 35° 2θ (using a step size of 0.05° 2θ and a step time of 2.0 seconds) or an angular range of 2° to 42° 2θ (using a step size of 0.025° 2θ and a step time of 5.0 seconds). Samples run under ambient conditions were prepared as flat plate specimens using powder as received without grinding. Approximately, 20 mg of the sample was gently packed into sample holder and all samples were analysed using Diffrac Plus EVA v4.2.0.14.

Thermal Analysis—Differential Scanning calorimetry (DSC): DSC data were collected on a PerkinElmer Pyris 4000 DSC equipped with a 45 position sample holder. The instrument was verified for energy and temperature calibration using certified indium. A predefined amount of the sample, 0.5-3.0 mg, was placed in a pin holed aluminium pan and heated at 20° C./min from 30 to 350° C. A purge of dry nitrogen at 60 ml/min was maintained over the sample. The instrument control, data acquisition and analysis were performed with Pyris Software v9.0.1.0203.

Thermo-Gravimetric Analysis (TGA): TGA data were collected on a PerkinElmer Pyris 1 TGA equipped with a 20 position auto-sampler. The instrument was calibrated using a certified weight and certified Alumel and Perkalloy for temperature. A predefined amount of the sample, 1-5 mg, was loaded onto a pre-tared aluminium crucible and was heated at 20° C./min from ambient temperature to 400° C. A nitrogen purge at 20 ml/min was maintained over the sample. The instrument control, data acquisition and analysis were performed with Pyris Software v9.0.1.0203.

Solution Proton NMR: $^1$H-NMR spectra were collected using a JEOL EX 270 MHz spectrometer equipped with an auto-sampler. The samples were dissolved in the appropriate deuterated solvent for analysis. The data was acquired using Delta NMR Processing and Control Software version 4.3.

FT-IR: FT-IR spectra were obtained using a Perkin Elmer Spectrum 2 spectrometer and collected between 450 cm$^{-1}$ and 4000 cm$^{-1}$ using 4 scans and a resolution of 4 cm$^{-1}$. A Universal ATR diamond accessory was used and the data were analyzed using software version NIOS2 main 00.02.0064.

Gravity Vapor Isotherm (GVS) Analysis: Sorption isotherms were obtained using a Hiden Isochema moisture sorption analyzer (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 ml/min. The instrument was verified for relative humidity content by measuring three calibrated Rotronic salt solutions (10-50-88%). The weight change of the sample was monitored as a function of humidity by a microbalance (accuracy +/−0.005 mg). A defined amount of sample was placed in a tared mesh stainless steel basket under ambient conditions. The sample was held at 50% RH for ~60 minutes and then the initial desorption cycle was initiated. A full experimental cycle typically consisted of three scans (desorption, sorption and desorption) at a constant temperature (25° C.) and 10% RH intervals over a 0-90% range (60 minutes for each humidity level). Data analysis was performed in Microsoft Excel.

Example 1. 1:1 Cannabidiolic Acid L-Phenylalanine Cocrystal 1.1 Preparation of a 1:1 Cannabidiolic L-Phenylalanine Cocrystal The batch of the 1:1 cannabidiolic L-phenylalanine cocrystal used for characterisation was prepared as follows: cannabidiolic acid (129 mg, 0.36 mmol) and L-phenylalanine (59 mg, 0.36 mmol) were milled together with nitromethane (1 drop) for 3×10 minutes at 30 Hz in a Retsch MM400 ball mill. The product was then dried in-vacuo at 40° C. for 1 hour.

1.2 XRPD Characterisation of a 1:1 Cannabidiolic Acid L-Phenylalanine Cocrystal

Figure 3:
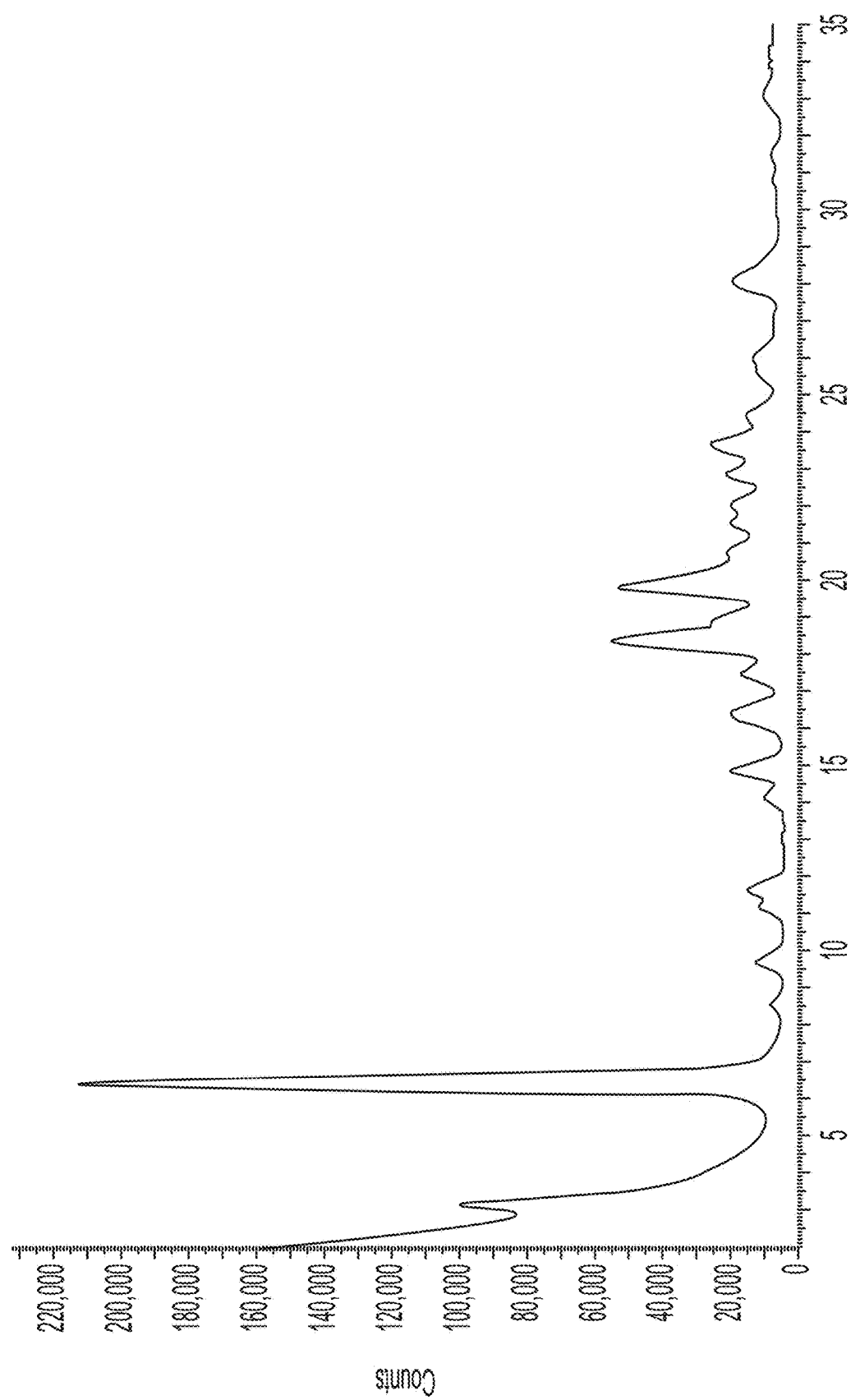
FIG. 3 depicts the XRPD diagram of the 1:1 cannabidiolic acid L-phenylalanine cocrystal, according to an exemplary embodiment.

The experimental XRPD pattern of the 1:1 cannabidiolic L-phenylalanine cocrystal is shown in FIG. 3. Table 1 lists the angles, °2θ+0.2 °2θ, and d-spacing of the peaks identified in the experimental XRPD pattern of FIG. 2. The entire list of peaks, or a subset thereof, may be sufficient to characterize the cocrystal, as well as by an XRPD pattern substantially similar to FIG. 2.

TABLE 1

| Angle °2θ ± 0.2 °2θ | d value Angstrom | Intensity % |
|---|---|---|
| 3.1 | 28.29 | 27% |
| 6.4 | 13.75 | 100% |
| 8.5 | 10.34 | 1% |
| 9.7 | 9.13 | 4% |
| 11.2 | 7.89 | 4% |
| 11.6 | 7.60 | 6% |
| 14.2 | 6.21 | 2% |
| 14.9 | 5.95 | 8% |
| 16.5 | 5.38 | 7% |
| 17.5 | 5.07 | 6% |
| 18.4 | 4.83 | 27% |
| 19.8 | 4.48 | 27% |
| 20.6 | 4.31 | 7% |
| 21.6 | 4.12 | 7% |
| 22.0 | 4.03 | 7% |
| 22.9 | 3.89 | 8% |
| 23.7 | 3.76 | 10% |
| 24.4 | 3.64 | 4% |
| 26.0 | 3.43 | 4% |
| 28.1 | 3.18 | 8% |

1.3 TGA of the 1:1 Cannabidiolic Acid L-Phenylalanine Cocrystal

Figure 4:
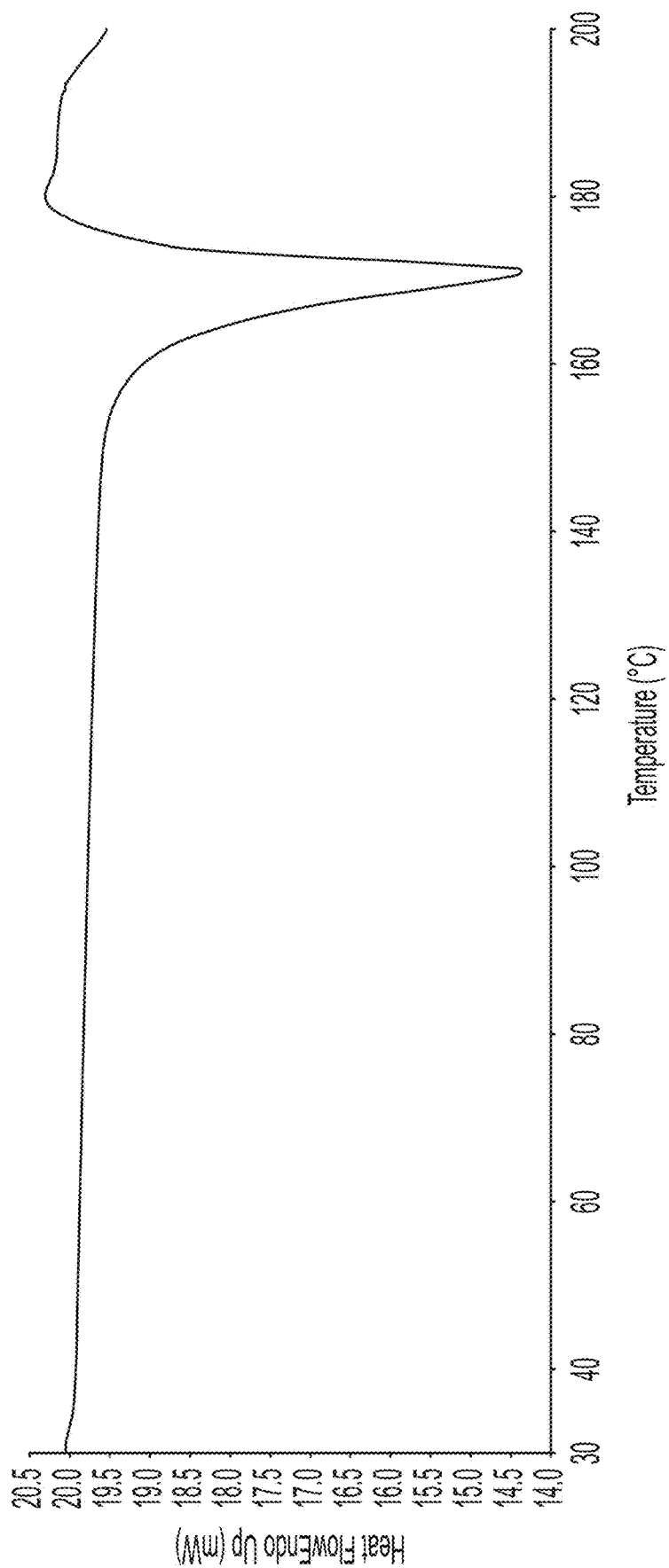
FIG. 4 depicts the differential scanning calorimetry (DSC) trace for the 1:1 cannabidiolic acid L-phenylalanine cocrystal, according to an exemplary embodiment.

The differential scanning calorimetry (DSC) trace, FIG. 4, shows a single endotherm with a peak maximum of 171.1° C.

1.4 TGA of the 1:1 Cannabidiolic Acid L-Phenylalanine Cocrystal

Figure 5:
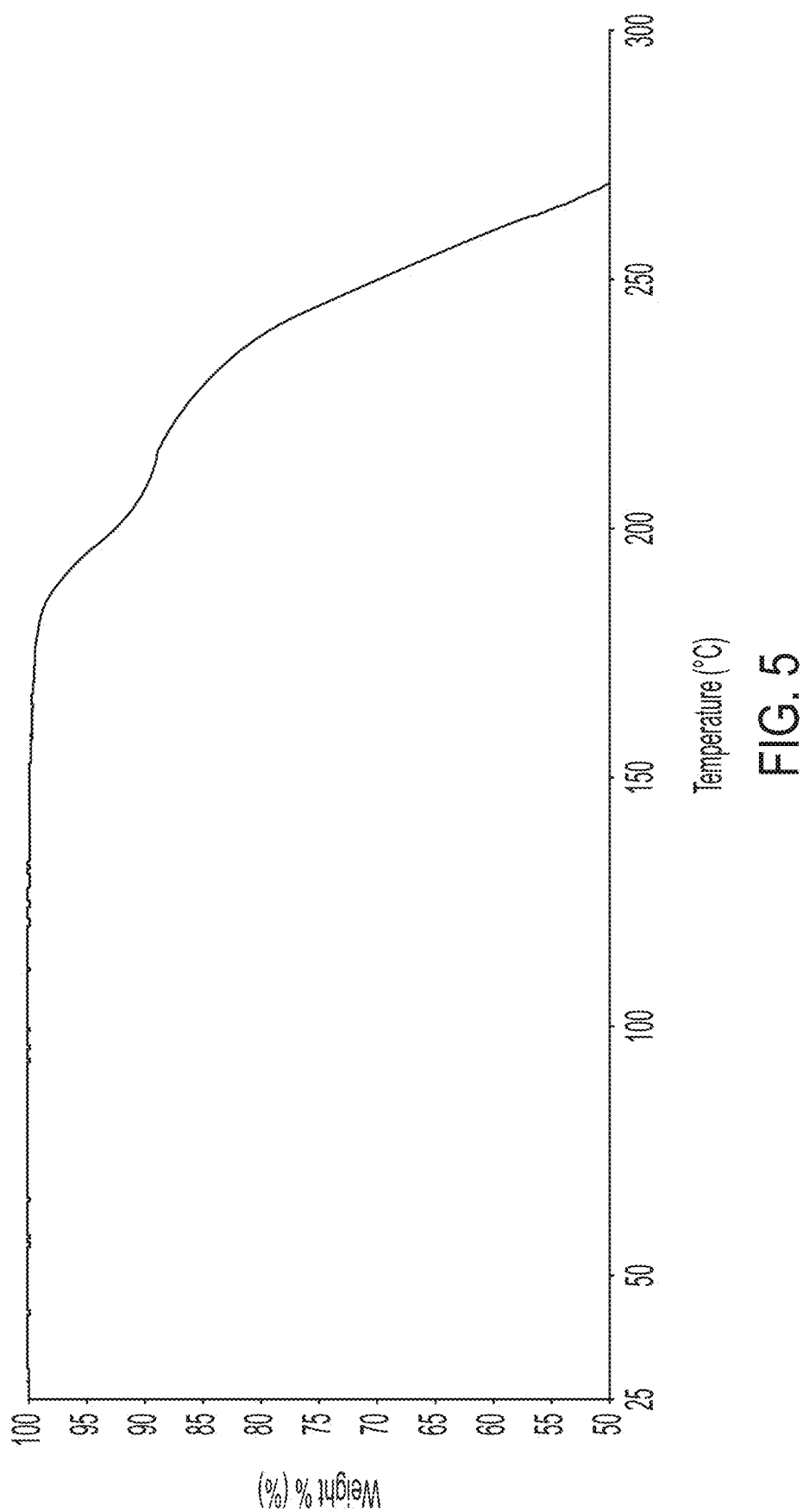
FIG. 5 depicts the thermogravimetric analysis (TGA) trace for the 1:1 cannabidiolic acid L-phenylalanine cocrystal, according to an exemplary embodiment.

The thermal gravimetric analysis (TGA) trace, FIG. 5, shows no significant weight loss prior to 175° C. A weight loss of approximately 9% can be seen over the temperature range 175-210° C. which is expected to be due to the decarboxylation of the CBDA following the melt of the cocrystal.

1.5 $^1$H NMR Spectrum of 1:1 Cannabidiolic Acid L-Phenylalanine Cocrystal

Figure 6:
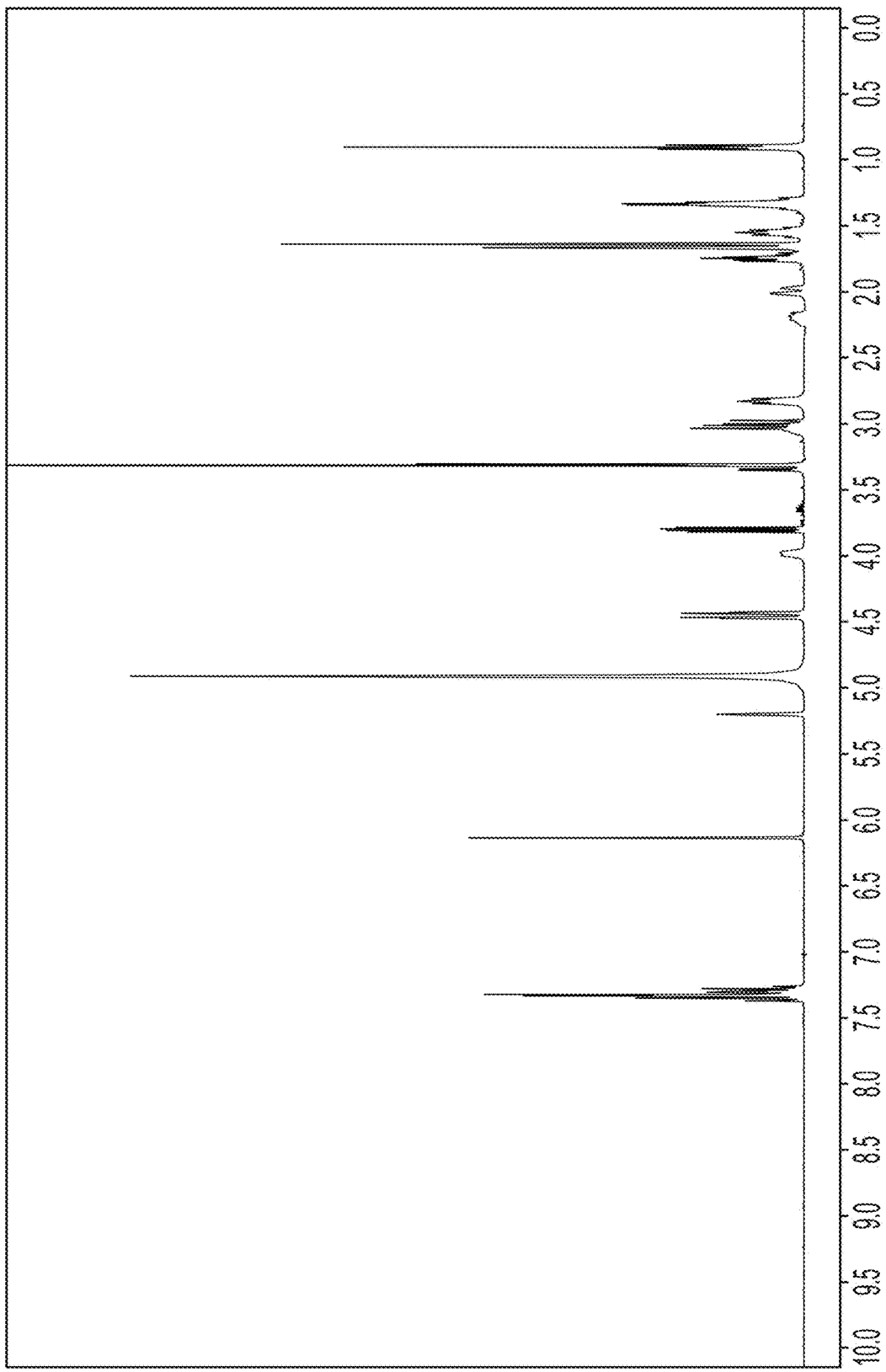
FIG. 6 depicts the 1H nuclear magnetic resonance (NMR) spectrum for the 1:1 cannabidiolic acid L-phenylalanine cocrystal, according to an exemplary embodiment.

The $^1$H NMR spectrum of the 1:1 cannabidiolic acid L-phenylalanine cocrystal, shown in FIG. 6, displays the following peaks: $^1$H NMR (400 MHz, MeOD) δ: 0.85-0.95 (3H), 1.28-1.39 (4H), 1.50-1.60 (2H), 1.64 (3H), 1.67 (3H), 1.70-1.78 (2H), 1.95-2.05 (1H), 2.15-2.25 (1H), 2.78-2.87 (2H), 2.95-3.10 (2H), 3.76-3.84 (1H), 3.92-4.04 (1H), 4.41-4.49 (2H), 5.20 (1H), 6.14 (1H) and 7.24-7.40 (5H). The peak at 3.76-3.84 ppm in the 1H NMR spectrum corresponds to one proton of L-phenylalanine. Comparison of the integration of this peak with that at 6.14 ppm, which corresponds to one of the aromatic protons of cannabidiolic acid, indicates that the cocrystal has an API: coformer stoichiometry of 1:1.

Figure 7:
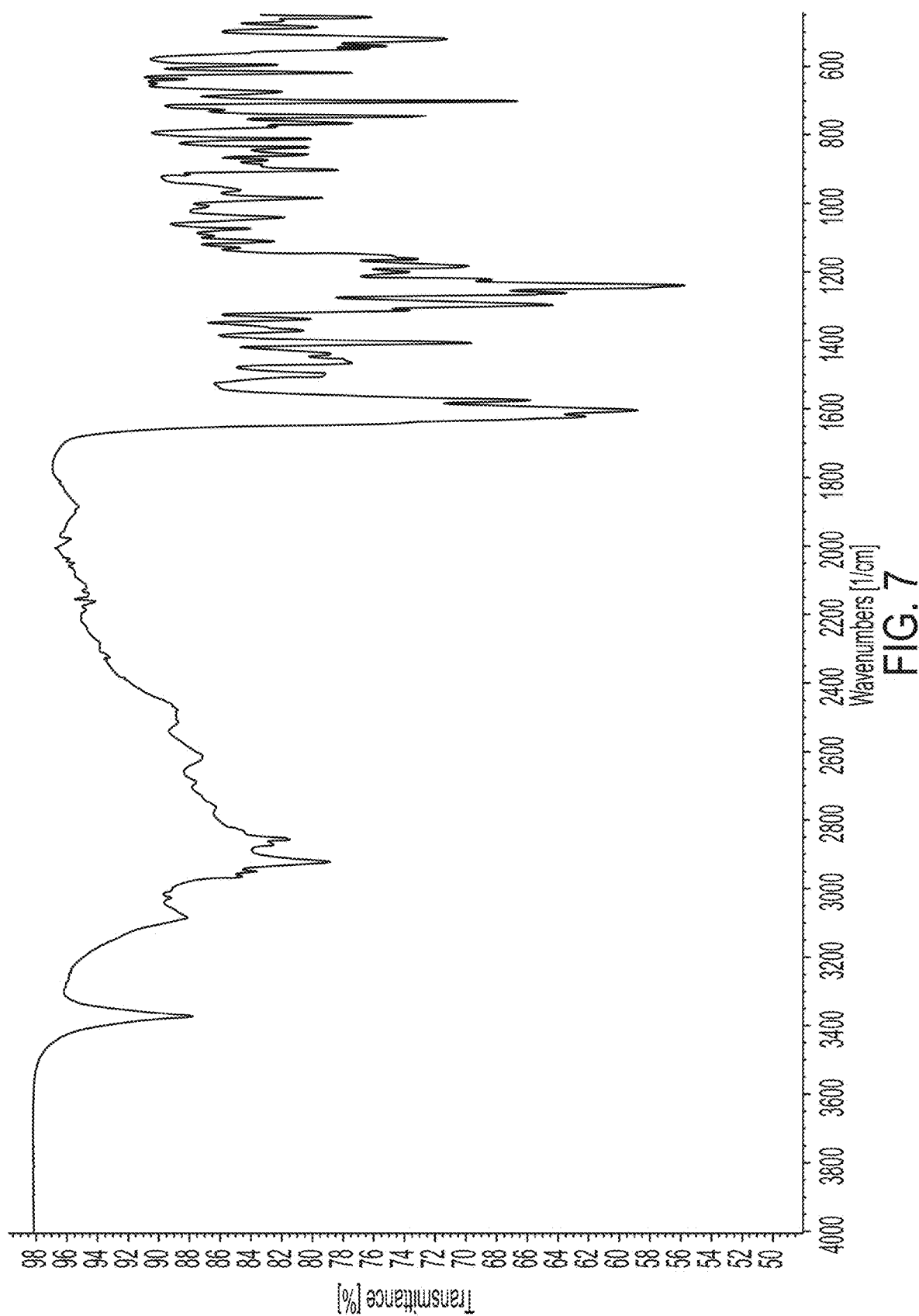
FIG. 7 depicts the infrared spectrum for the 1:1 cannabidiolic acid L-phenylalanine cocrystal, according to an exemplary embodiment.

1.6 Infrared Spectrum of the 1:1 Cannabidiolic Acid L-Phenylalanine Cocrystal The experimental infrared Spectrum of the 1:1 cannabidiolic acid L-phenylalanine cocrystal is shown in FIG. 7. The significant peaks identified in the experimental infrared spectrum of FIG. 6 are 3374, 3085, 2923, 2857, 1622, 1606, 1576, 1498, 1466, 1441, 1409, 1370, 1337, 1296, 1263, 1240, 1200, 1184, 1163, 1112, 1076, 1041, 986, 963, 904, 859, 838, 814, 767, 747, 702, 674, 619, 598, 521, 485 and 457 cm$^{-1}$±1 cm$^{-1}$. The entire list of peaks, or a subset thereof, may be sufficient to characterize the cocrystal, as well as by an infrared pattern substantially similar to FIG. 7. For example, the 1:1 cannabidiolic acid L-phenylalanine cocrystal may be characterized by at least three peaks selected from the peaks at 1606, 1409, 1296, 1240 and 1184 cm$^{-1}$±1 cm$^{-1}$.

Example 2. 1:1 Cannabidiolic Acid Vanillin Cocrystal

2.1 Preparation of a 1:1 Cannabidiolic Vanillin Cocrystal

The batch of the 1:1 cannabidiolic vanillin cocrystal used for characterisation was prepared as follows: Cannabidiolic acid (137 mg, 0.38 mmol) and Vanillin (56 mg, 0.37 mmol) were weighed into a glass vial and vanillin saturated nitromethane (1 ml) was added. The resulting slurry was stirred at 5° C. for 3 hours. The product was then filtered under vacuum and dried in-vacuo at 30° C. for 3 hours.

2.2 XRPD Characterisation of a 1:1 Cannabidiolic acid Vanillin Cocrystal

Figure 8:
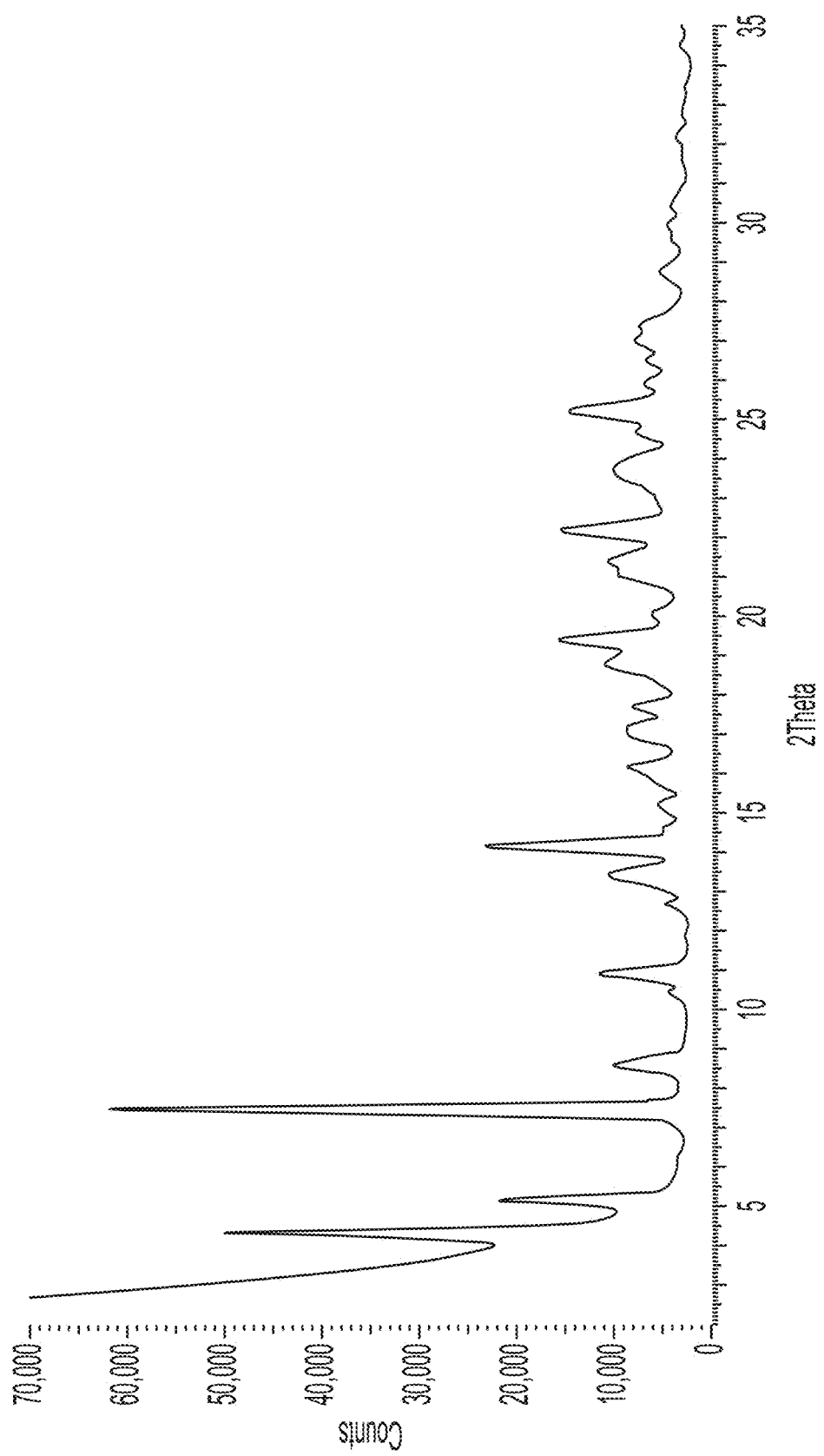
FIG. 8 depicts the XRPD diagram of the 1:1 cannabidiolic acid vanillin cocrystal, according to an exemplary embodiment.

The experimental XRPD pattern of the 1:1 cannabidiolic vanillin cocrystal is shown in FIG. 8. Table 2 lists the angles, °2θ+0.2 °2θ, and d-spacing of the peaks identified in the experimental XRPD pattern of FIG. 8. The entire list of peaks, or a subset thereof, may be sufficient to characterize the cocrystal, as well as by an XRPD pattern substantially similar to FIG. 8.

TABLE 2

| Angle °2θ ± 0.2 °2θ | d value Angstrom | Intensity % |
|---|---|---|
| 4.3 | 20.42 | 46% |
| 5.2 | 17.09 | 21% |
| 7.5 | 11.8 | 100% |
| 8.6 | 10.27 | 12% |
| 10.9 | 8.09 | 15% |
| 13.5 | 6.58 | 13% |
| 14.2 | 6.24 | 37% |
| 15.2 | 5.82 | 3% |
| 16.2 | 5.48 | 8% |
| 17.7 | 5.00 | 8% |
| 18.8 | 4.72 | 13% |
| 19.4 | 4.57 | 22% |
| 20.1 | 4.42 | 4% |
| 22.2 | 4.00 | 22% |
| 23.7 | 3.76 | 12% |
| 25.2 | 3.53 | 20% |
| 28.8 | 3.10 | 4% |

2.3 DSC of the 1:1 Cannabidiolic Acid Vanillin Cocrystal

Figure 9:
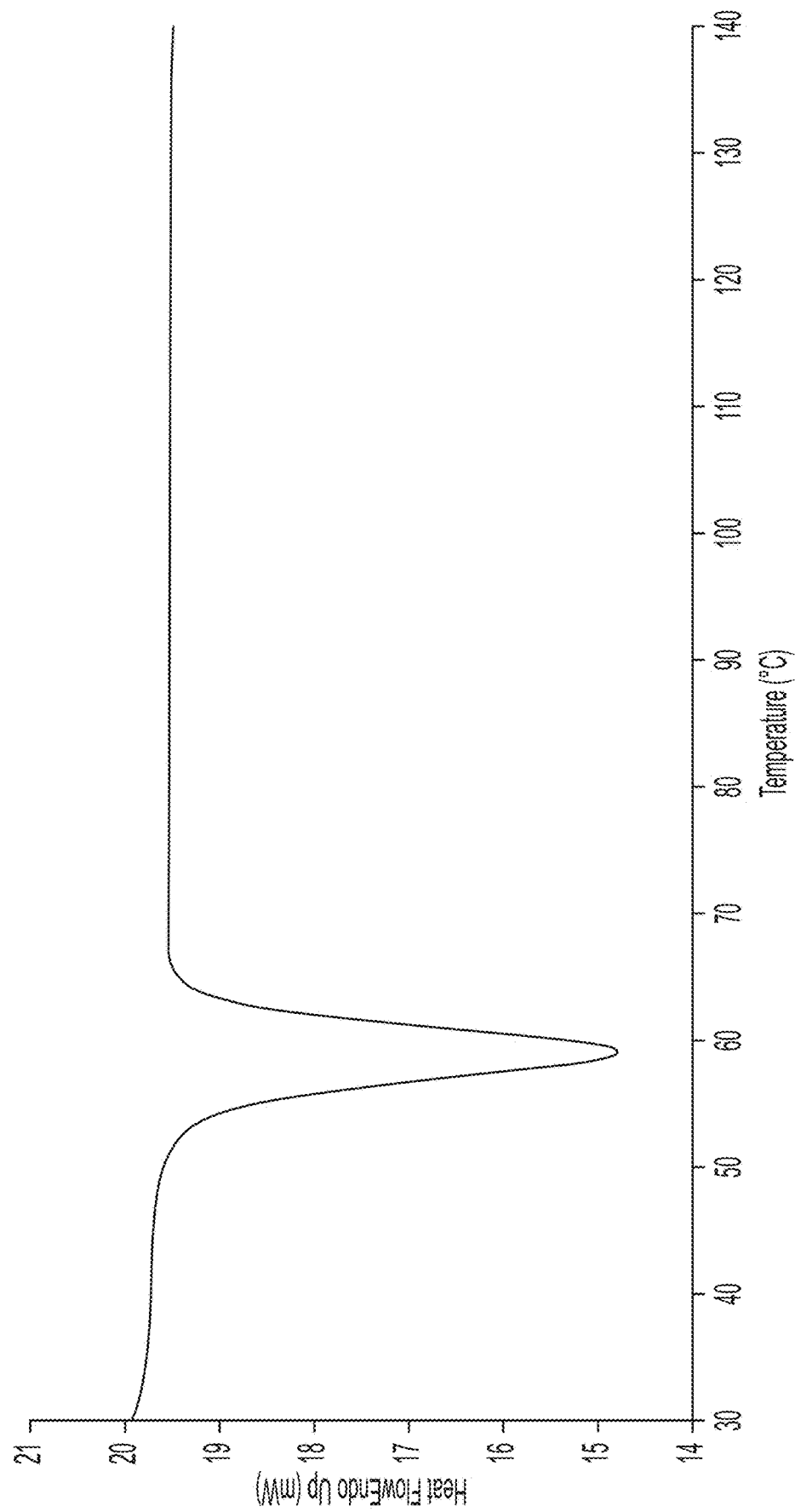
FIG. 9 depicts the DSC trace for the 1:1 cannabidiolic acid vanillin cocrystal, according to an exemplary embodiment.

The differential scanning calorimetry (DSC) trace, FIG. 9, shows a single endotherm with a peak maximum of 59.2° C.

2.4 TGA of the 1:1 Cannabidiolic Acid Vanillin Cocrystal

Figure 10:
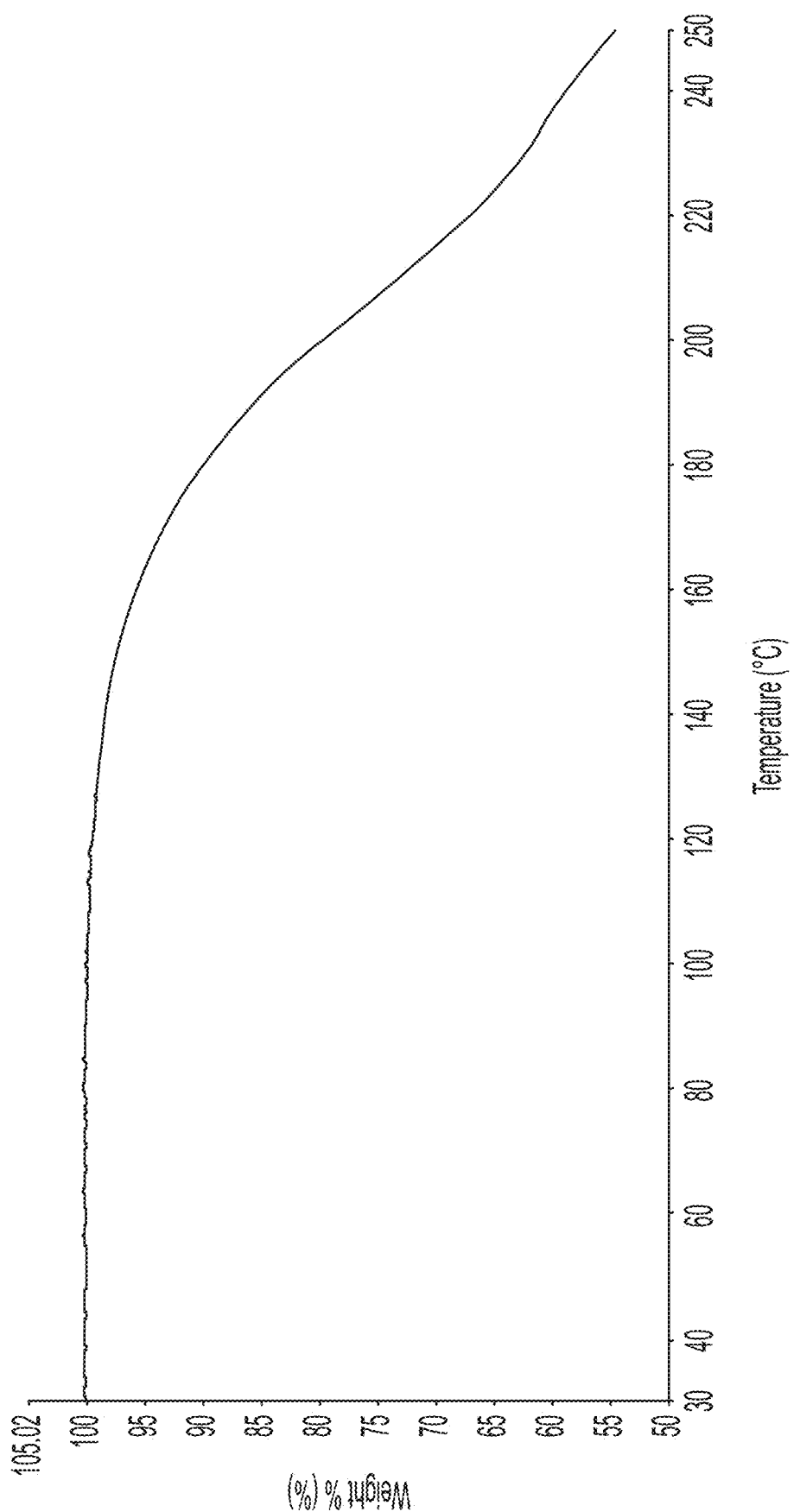
FIG. 10 depicts the TGA trace for the 1:1 cannabidiolic acid vanillin cocrystal, according to an exemplary embodiment.

The thermal gravimetric analysis (TGA) trace, FIG. 10, shows no significant weight loss prior to 120° C.

2.5 $^1$H NMR Spectrum of 1:1 Cannabidiolic Acid Vanillin Cocrystal

Figure 11:
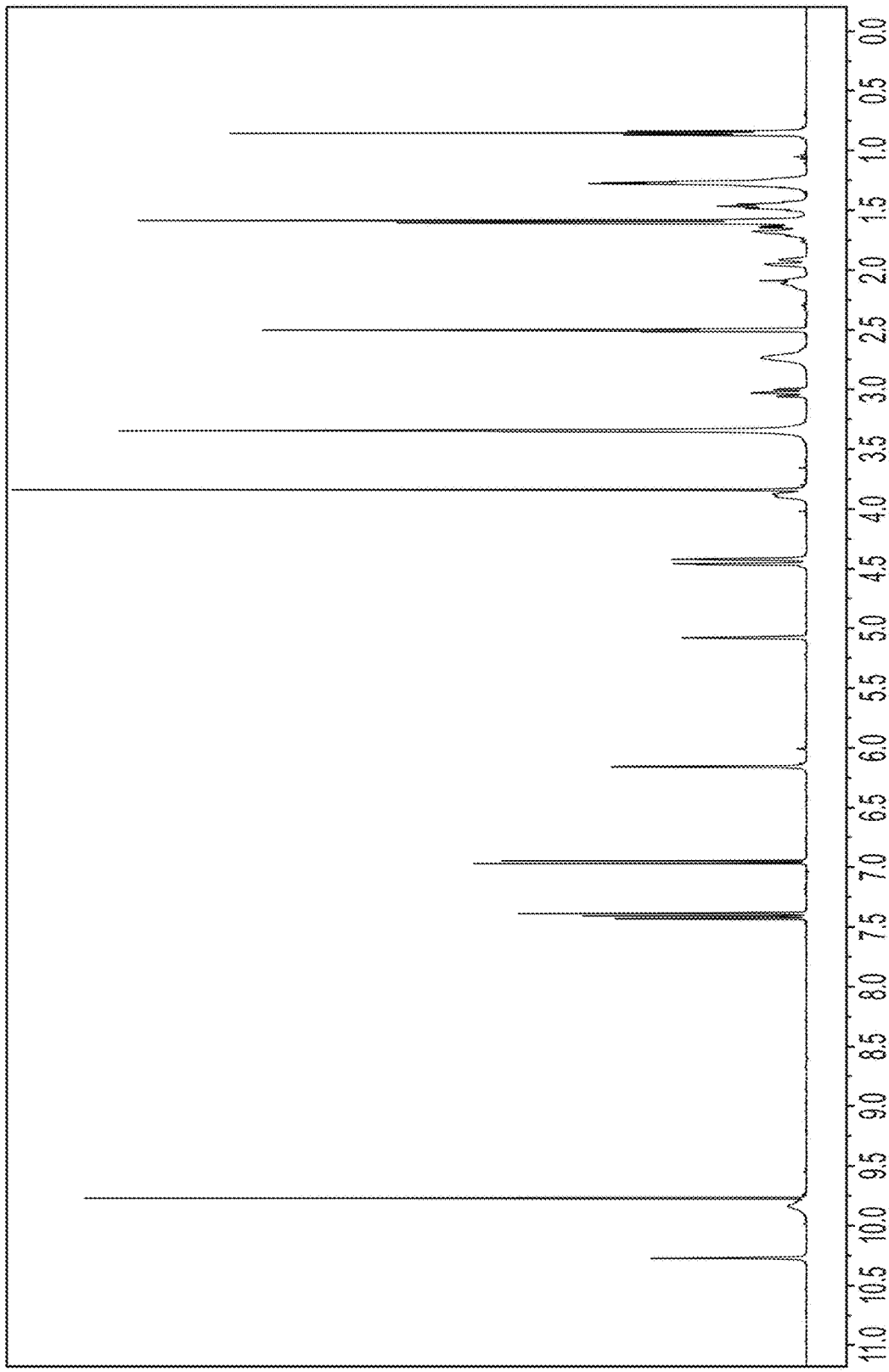
FIG. 11 depicts the 1H NMR spectrum for the 1:1 cannabidiolic acid vanillin cocrystal, according to an exemplary embodiment.

The 1H NMR spectrum of the 1:1 cannabidiolic acid vanillin cocrystal, shown in FIG. 11, displays the following peaks: $^1$H NMR (400 MHz, DMSO) δ: 0.80-0.89 (3H), 1.21-1.35 (4H), 1.40-1.52 (2H), 1.59 (3H), 1.60 (3H), 1.62-1.71 (2H), 1.88-1.98 (1H), 2.04-2.17 (1H), 2.63-2.85 (2H), 2.95-3.10 (1H), 3.84 (3H), 3.85-3.92 (1H), 4.36-4.47 (2H), 5.08 (1H), 6.15 (1H), 6.96 (1H), 7.35-7.45 (2H), 9.77 (1H) and 10.27 (1H). The peak at 3.84 ppm in the 1H NMR spectrum corresponds to the 3 protons of the methoxy group of vanillin. Comparison of the integration of this peak with that at 6.15 ppm, which corresponds to one of the aromatic protons of cannabidiolic acid, indicates that the cocrystal has an API: coformer stoichiometry of 1:1.

2.6 Infrared Spectrum of the 1:1 Cannabidiolic Acid Vanillin Cocrystal

Figure 12:
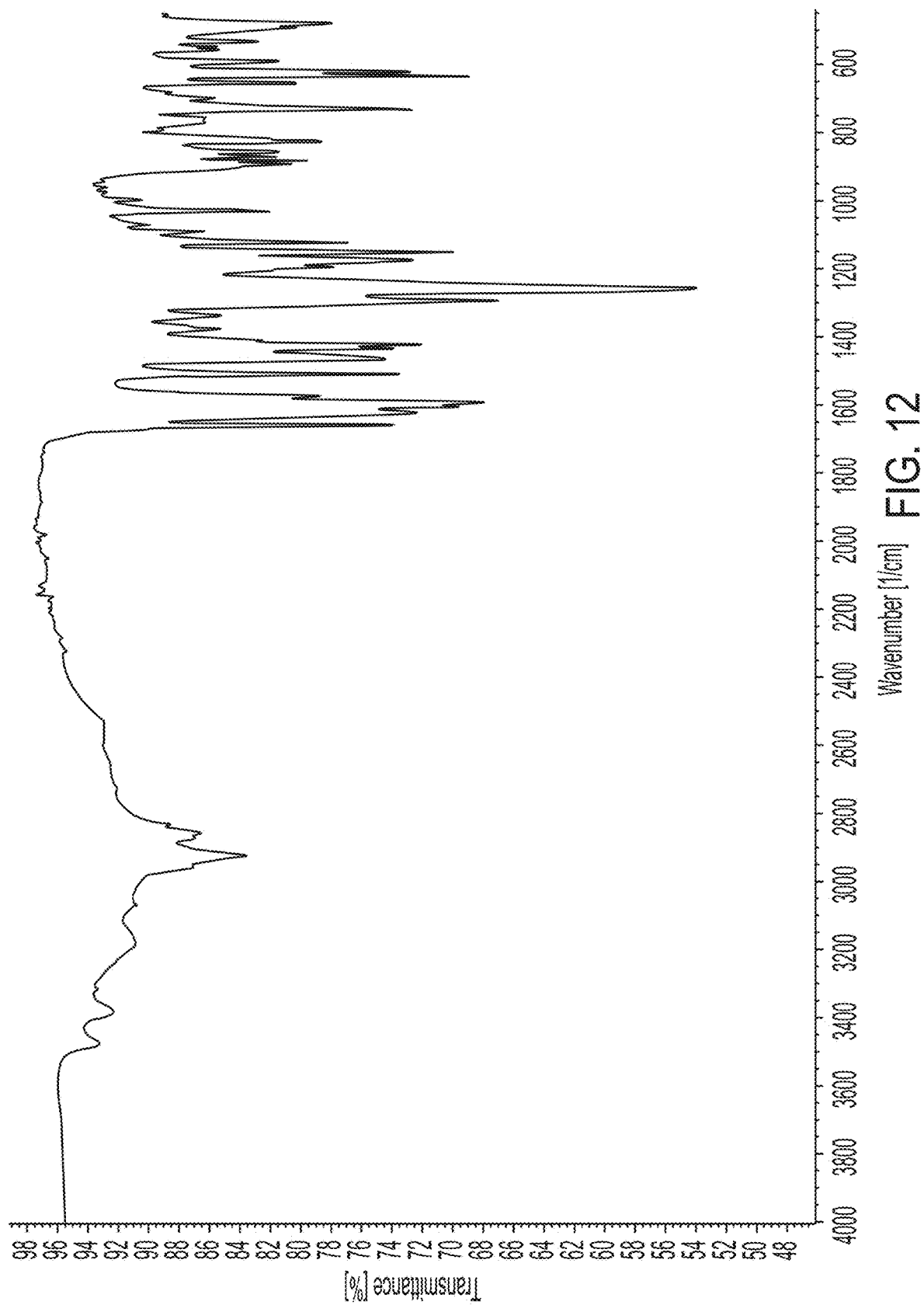
FIG. 12 depicts the infrared spectrum for the 1:1 cannabidiolic acid vanillin cocrystal, according to an exemplary embodiment.

The experimental infrared Spectrum of the 1:1 cannabidiolic acid vanillin cocrystal is shown in FIG. 12. The significant peaks identified in the experimental infrared spectrum of FIG. 11 are 3476, 3383, 2924, 2858, 1659, 1623, 1593, 1574, 1509, 1464, 1423, 1377, 1337, 1294, 1258, 1174, 1151, 1124, 1091, 1028, 997, 882, 857, 827, 770, 756, 731, 699, 655, 634, 622, 591, 533 and 479 cm$^{-1}$±1 cm$^{-1}$. The entire list of peaks, or a subset thereof, may be sufficient to characterize the cocrystal, as well as by an infrared pattern substantially similar to FIG. 12. For example, the 1:1 cannabidiolic acid vanillin cocrystal may be characterized by at least three peaks selected from the peaks at 1658, 1509, 1294, 1258 and 1151 cm$^{-1}$±1 cm$^{-1}$.

Example 3. 1:1 Cannabidiolic acid Betaine Cocrystal

3.1 Preparation of a 1:1 Cannabidiolic Betaine Cocrystal

The batch of the 1:1 cannabidiolic vanillin cocrystal used for characterisation was prepared as follows: Cannabidiolic acid (125 mg, 0.35 mmol) and betaine (59 mg, 0.36 mmol) were milled together with nitromethane (1 drop) for 3×10 minutes at 30 Hz in a Retsch MM400 ball mill. The product was then dried in-vacuo at 40° C. for 1 hour.

3.2 XRPD Characterisation of a 1:1 Cannabidiolic Acid Betaine Cocrystal

Figure 13:
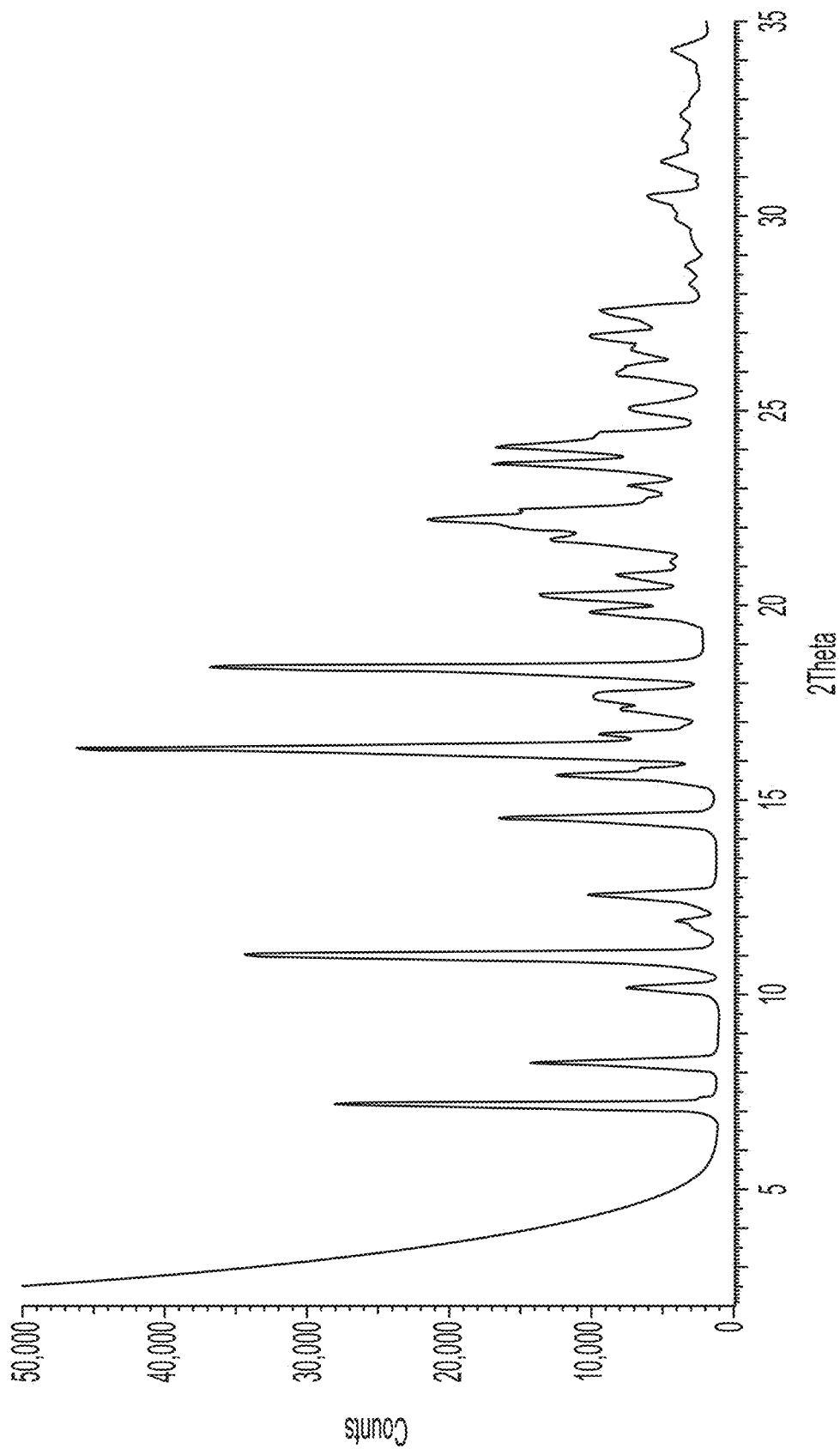
FIG. 13 depicts the XRPD diagram of the 1:1 cannabidiolic acid betaine cocrystal, according to an exemplary embodiment.

The experimental XRPD pattern of the 1:1 cannabidiolic betaine cocrystal is shown in FIG. 13. Table 3 lists the angles, °2θ±0.2 °2θ, and d-spacing of the peaks identified in the experimental XRPD pattern of FIG. 13. The entire list of peaks, or a subset thereof, may be sufficient to characterize the cocrystal, as well as by an XRPD pattern substantially similar to FIG. 13.

TABLE 3

| Angle °2θ ± 0.2 °2θ | d value Angstrom | Intensity % |
| --- | --- | --- |
| 7.2 | 12.28 | 54% |
| 8.3 | 10.71 | 27% |
| 10.2 | 8.68 | 13% |
| 11.0 | 8.03 | 70% |
| 11.9 | 7.44 | 6% |
| 12.5 | 7.05 | 19% |
| 14.5 | 6.09 | 34% |
| 15.6 | 5.66 | 24% |
| 16.3 | 5.43 | 100% |
| 16.7 | 5.31 | 26% |
| 17.3 | 5.12 | 22% |
| 17.6 | 5.03 | 18% |
| 18.4 | 4.81 | 81% |
| 19.8 | 4.47 | 28% |
| 20.3 | 4.38 | 27% |
| 20.8 | 4.27 | 14% |
| 21.7 | 4.09 | 24% |
| 22.2 | 4.00 | 45% |
| 23.1 | 3.85 | 17% |
| 23.6 | 3.76 | 50% |
| 24.1 | 3.70 | 34% |
| 25.1 | 3.55 | 11% |
| 26.1 | 3.41 | 11% |
| 26.9 | 3.31 | 18% |
| 27.6 | 3.23 | 16% |

3.3 DSC of the 1:1 Cannabidiolic Acid Betaine Cocrystal

Figure 14:
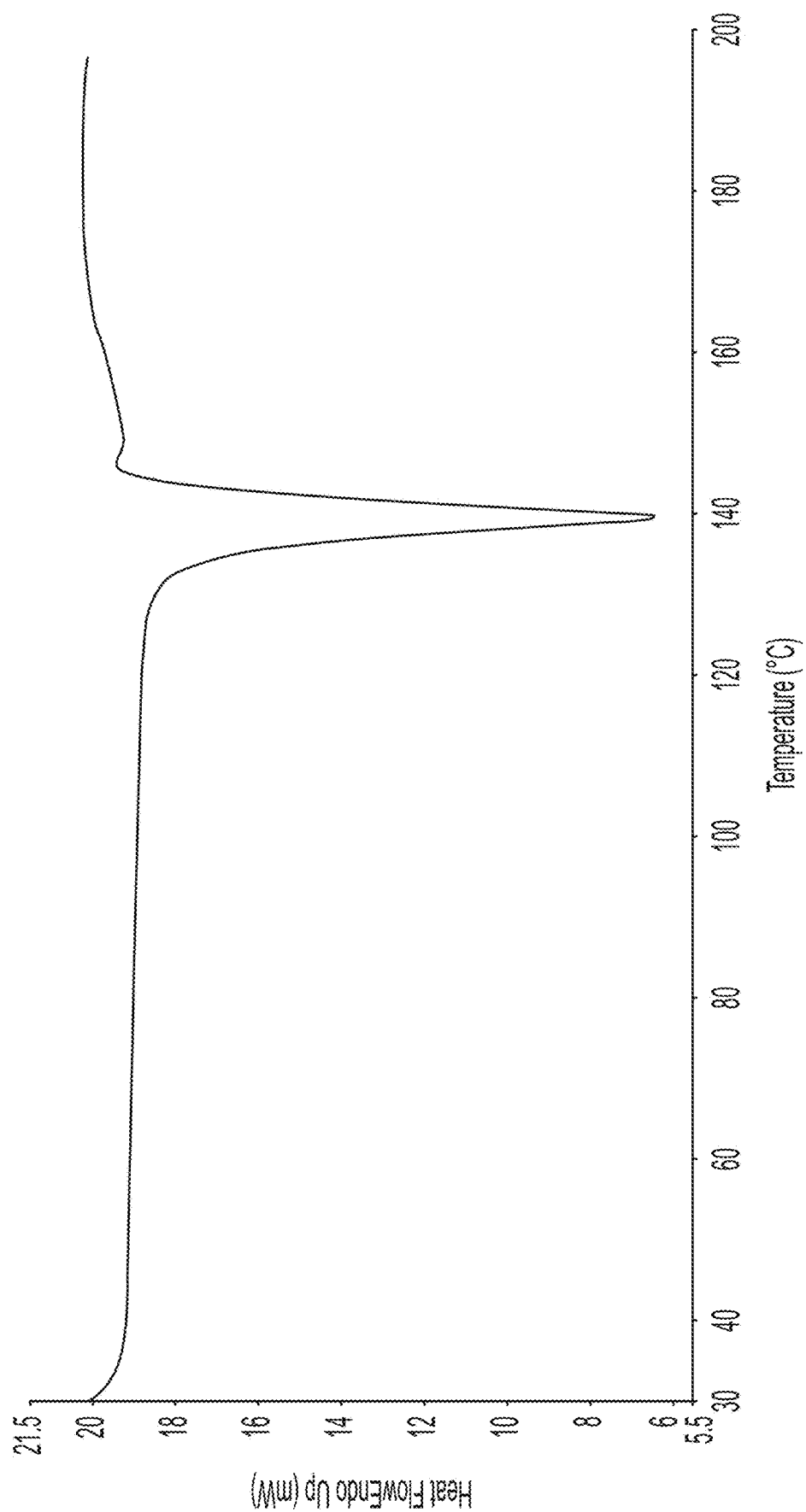
FIG. 14 depicts the DSC trace for the 1:1 cannabidiolic acid betaine cocrystal, according to an exemplary embodiment.

The differential scanning calorimetry (DSC) trace, FIG. 14, shows a single endotherm with a peak maximum of 139.7° C.

3.4 TGA of the 1:1 Cannabidiolic Acid Betaine Cocrystal

Figure 15:
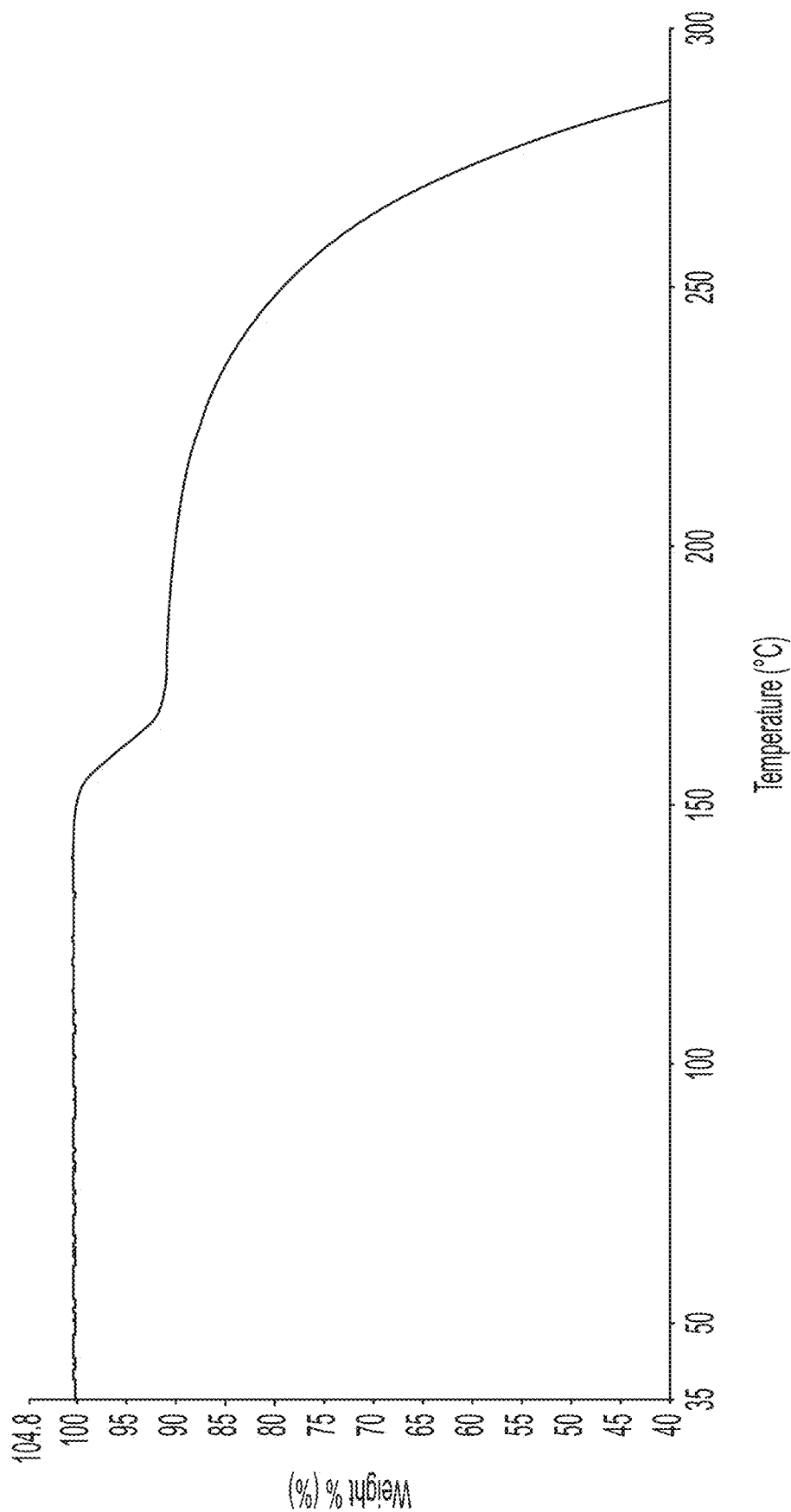
FIG. 15 depicts the TGA trace for the 1:1 cannabidiolic acid betaine cocrystal, according to an exemplary embodiment.

The thermal gravimetric analysis (TGA) trace, FIG. 15, shows no significant weight loss prior to 150° C. A weight loss of approximately 10% can be seen over the temperature range 150-170° C. which is expected to be due to the decarboxylation of the CBDA following the melt of the cocrystal.

3.5 $^1$H NMR Spectrum of 1:1 Cannabidiolic Acid Betaine Cocrystal

Figure 16:
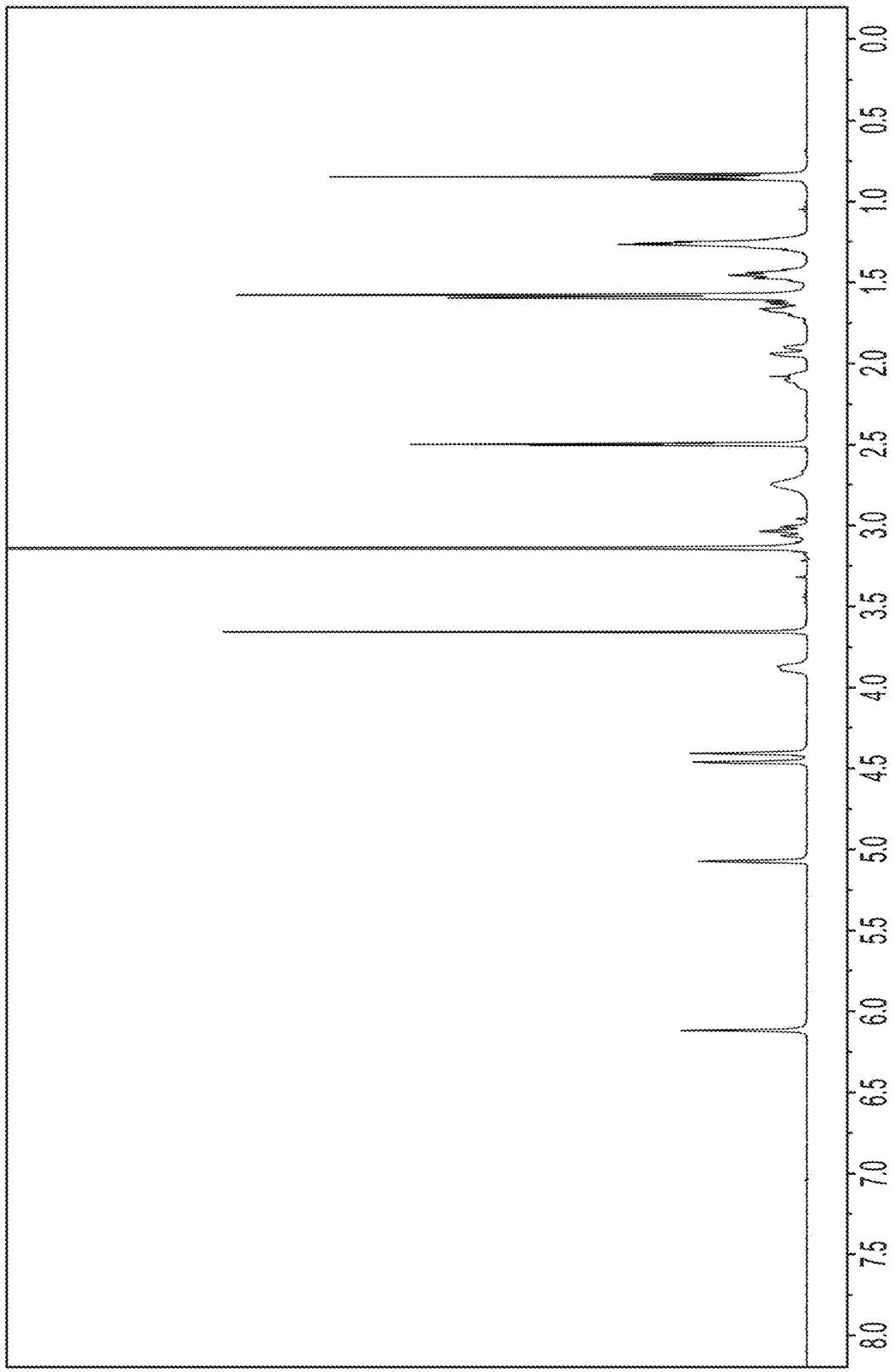
FIG. 16 depicts the 1H NMR spectrum for the 1:1 cannabidiolic acid betaine cocrystal, according to an exemplary embodiment.

The $^1$H NMR spectrum of the 1:1 cannabidiolic acid betaine cocrystal, shown in FIG. 16, displays the following peaks: $^1$H NMR (400 MHz, DMSO) δ: 0.80-0.89 (3H), 1.21-1.35 (4H), 1.40-1.52 (2H), 1.59 (3H), 1.60 (3H), 1.62-1.71 (2H), 1.88-1.98 (1H), 2.04-2.17 (1H), 2.63-2.85 (2H), 2.95-3.10 (1H), 3.14 (9H), 3.66 (2H), 3.85-3.92 (1H), 4.36-4.47 (2H), 5.08 (1H) and 6.12 (1H). The peak at 3.66 ppm in the 1H NMR spectrum corresponds to two protons of betaine. Comparison of the integration of this peak with that at 6.12 ppm, which corresponds to one of the aromatic protons of cannabidiolic acid, indicates that the cocrystal has an API: coformer stoichiometry of 1:1.

3.6 Infrared Spectrum of the 1:1 Cannabidiolic Acid Betaine Cocrystal

Figure 17:
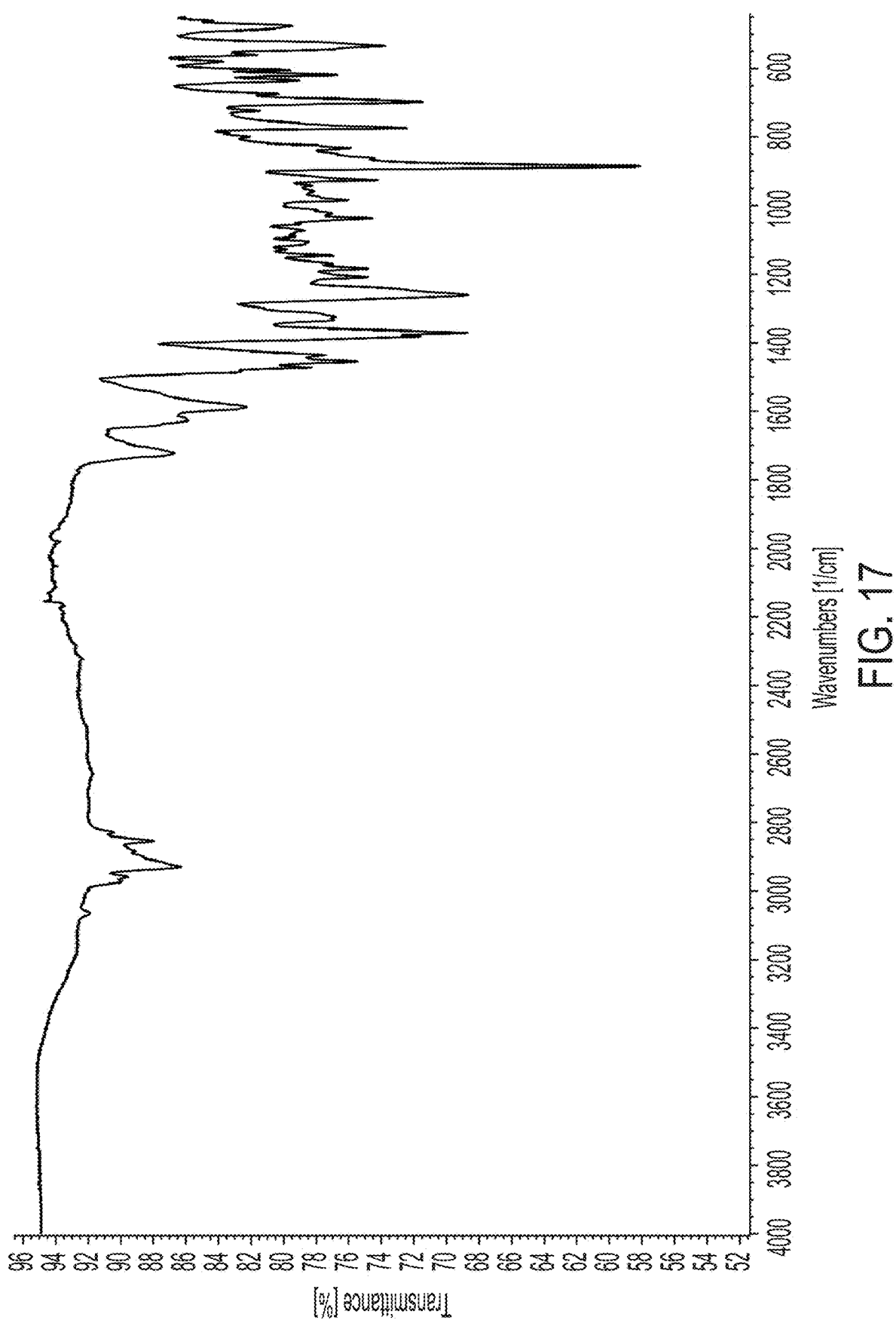
FIG. 17 depicts the infrared spectrum for the 1:1 cannabidiolic acid betaine cocrystal, according to an exemplary embodiment.

The experimental infrared spectrum of the 1:1 cannabidiolic acid betaine cocrystal is shown in FIG. 17. The significant peaks identified in the experimental infrared spectrum of FIG. 17 are 3067, 2960, 2390, 2855, 1723, 1627, 1589, 1474, 1456, 1437, 1371, 1325, 1261, 1210, 1185, 1147, 1106, 1037, 985, 927, 887, 833, 773, 723, 697, 634, 619, 605, 581, 534 and 477 cm$^{-1}$±1 cm$^{-1}$. The entire list of peaks, or a subset thereof, may be sufficient to characterize the cocrystal, as well as by an infrared pattern substantially similar to FIG. 17. For example, the 1:1 cannabidiolic acid betaine cocrystal may be characterized by at least three peaks selected from the peaks at 1723, 1589, 1371, 1261 and 887 cm$^{-1}$±1 cm$^{-1}$.

Example 4: 1:1 Cannabidiolic Acid Ethyl Maltol Cocrystal

4.1 Preparation of a 1:1 Cannabidiolic Ethyl Maltol Cocrystal

The batch of the 1:1 cannabidiolic ethyl maltol cocrystal used for characterisation was prepared as follows: Cannabidiolic acid (54 mg, 0.15 mmol) and ethyl maltol (18 mg, 0.13 mmol) were weighed into a glass vial and vanillin saturated cyclohexane (1 ml) was added. The resulting slurry was placed in a shaker and matured for 48 hours (room temperature to 40° C. on an 8 hour cycle, heating to 40° C. for 4 hours and then cooling to RT for a further 4 hours) before being stirred at 5° C. for 3 hours. The product was then filtered under vacuum and dried in-vacuo at 30° C. for 3 hours.

Figure 18:
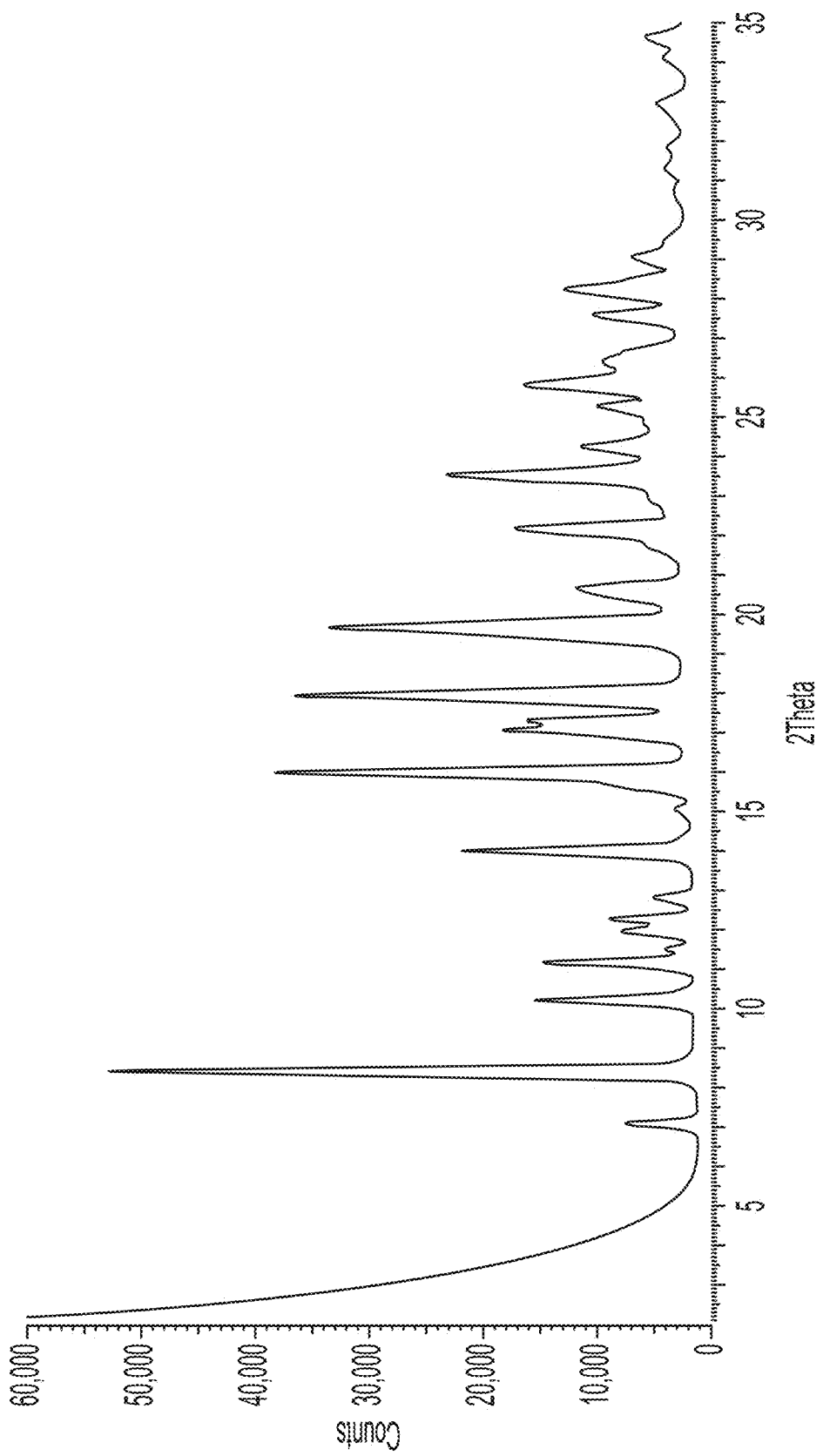
FIG. 18 depicts the XRPD diagram of the 1:1 cannabidiolic acid ethyl maltol cocrystal, according to an exemplary embodiment.

4.2 XRPD Characterisation of a 1:1 Cannabidiolic Acid Ethyl Maltol Cocrystal The experimental XRPD pattern of the 1:1 cannabidiolic ethyl maltol cocrystal is shown in FIG. 18. Table 4 lists the angles, °2θ±0.2 °2θ, and d-spacing of the peaks identified in the experimental XRPD pattern of FIG. 18. The entire list of peaks, or a subset thereof, may be sufficient to characterize the cocrystal, as well as by an XRPD pattern substantially similar to FIG. 18.

TABLE 4

| Angle °2θ ± 0.2 °2θ | d value Angstrom | Intensity % |
| --- | --- | --- |
| 7.1 | 12.41 | 11% |
| 8.4 | 10.46 | 100% |
| 10.2 | 8.63 | 27% |
| 11.2 | 7.90 | 26% |
| 12.0 | 7.38 | 21% |
| 12.3 | 7.19 | 14% |
| 12.8 | 6.89 | 7% |
| 14.0 | 6.31 | 41% |
| 16.0 | 5.53 | 77% |
| 17.1 | 5.19 | 59% |
| 17.3 | 5.12 | 46% |
| 18.0 | 4.94 | 73% |
| 19.7 | 4.51 | 65% |
| 20.7 | 4.29 | 19% |
| 22.2 | 4.00 | 31% |
| 23.5 | 3.78 | 45% |
| 25.3 | 3.52 | 15% |
| 25.8 | 3.45 | 29% |
| 26.4 | 3.37 | 13% |
| 27.6 | 3.23 | 16% |
| 28.3 | 3.16 | 22% |
| 29.1 | 3.07 | 9% |

4.3 DSC of the 1:1 Cannabidiolic Acid Ethyl Maltol Cocrystal

Figure 19:
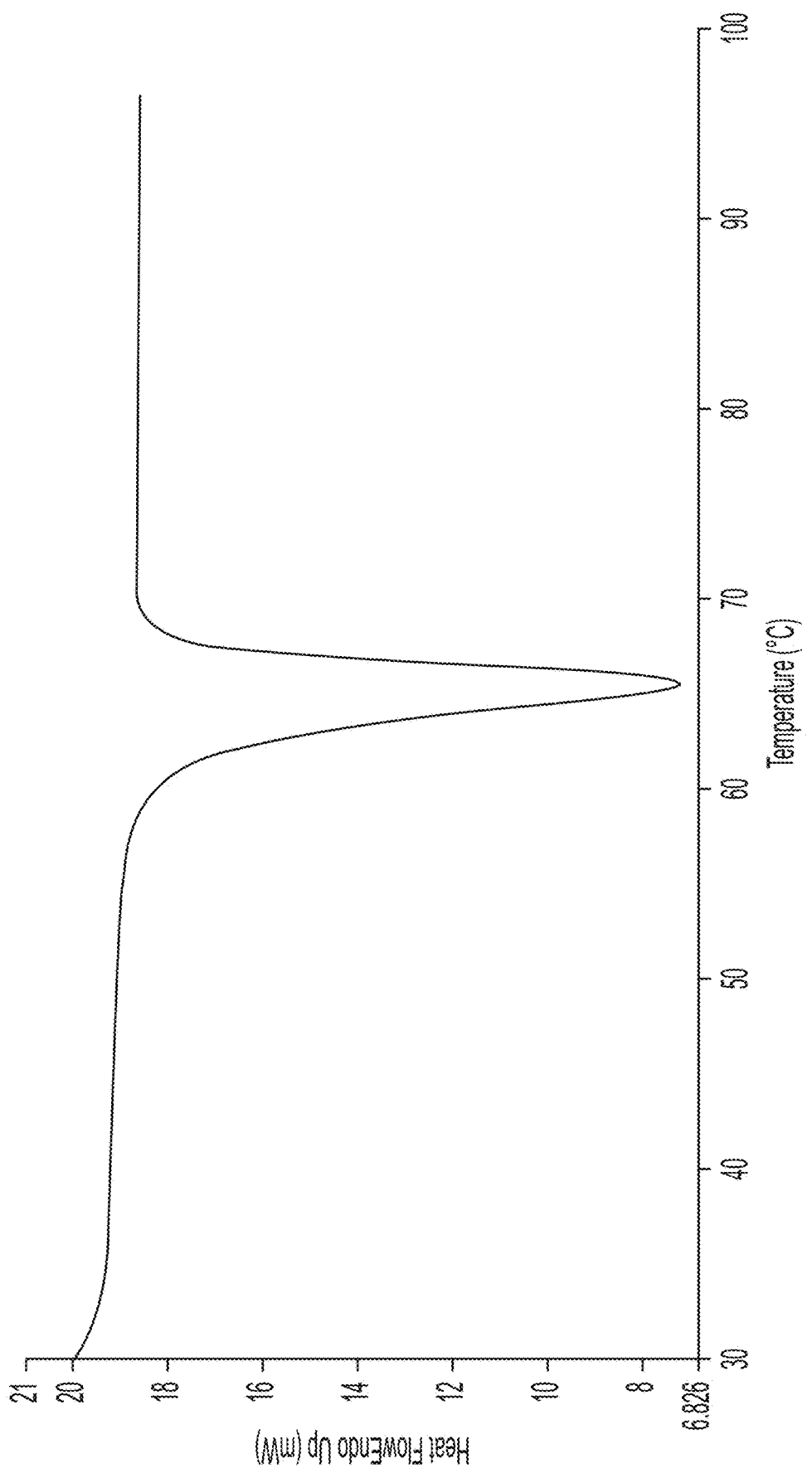
FIG. 19 depicts the DSC trace for the 1:1 cannabidiolic acid ethyl maltol cocrystal, according to an exemplary embodiment.

The differential scanning calorimetry (DSC) trace, FIG. 19, shows a single endotherm with a peak maximum of 65.6° C.

4.4 TGA of the 1:1 Cannabidiolic Acid Ethyl Maltol Cocrystal

Figure 20:
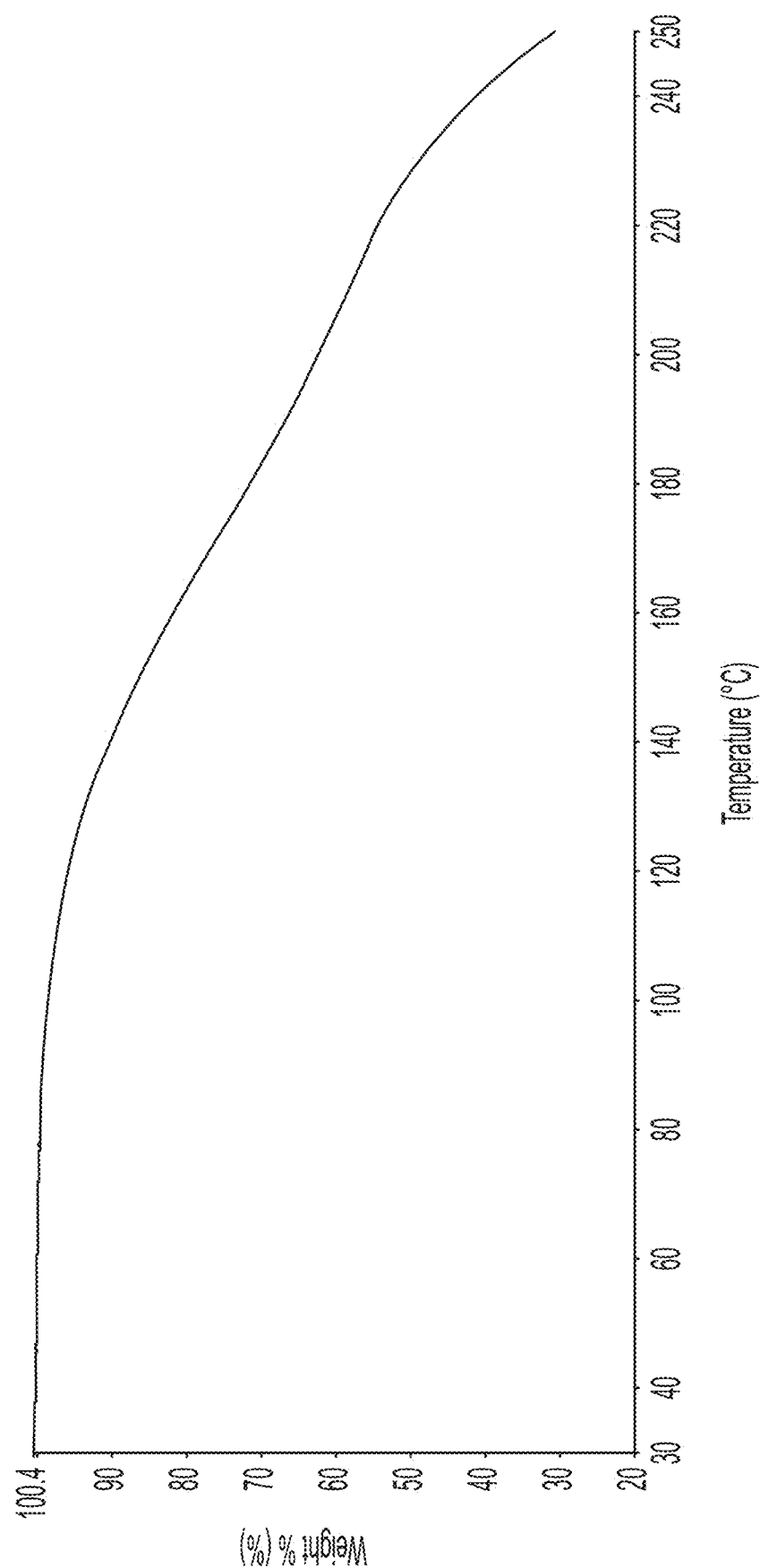
FIG. 20 depicts the TGA trace for the 1:1 cannabidiolic acid ethyl maltol cocrystal, according to an exemplary embodiment.

The thermal gravimetric analysis (TGA) trace, FIG. 20, shows no significant weight loss prior to 70° C.

4.5 $^1$H NMR Spectrum of 1:1 Cannabidiolic Acid Ethyl Maltol Cocrystal

Figure 21:
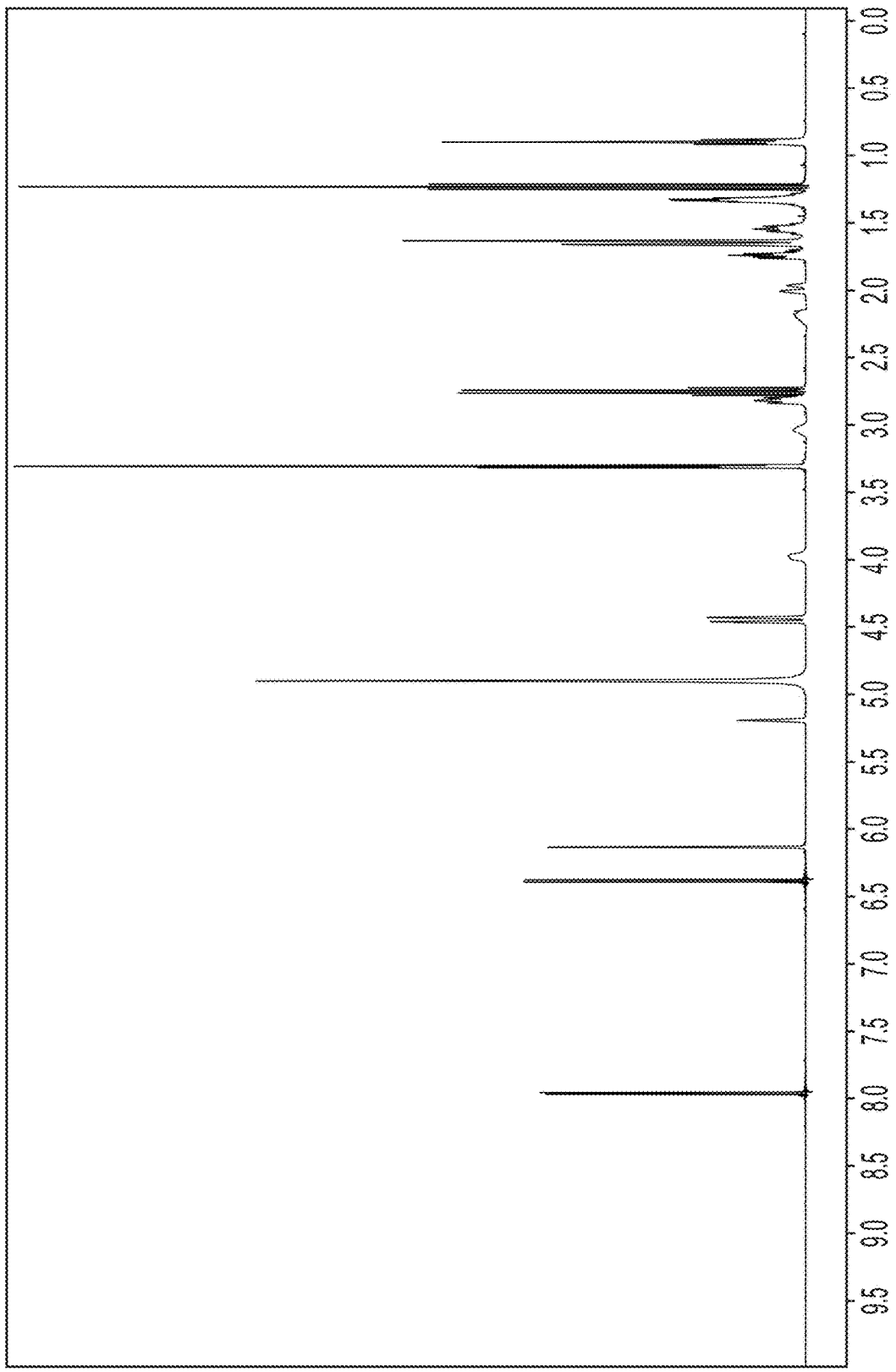
FIG. 21 depicts the 1H NMR spectrum for the 1:1 cannabidiolic acid ethyl maltol cocrystal, according to an exemplary embodiment.

The $^1$H NMR spectrum of the 1:1 cannabidiolic acid ethyl maltol cocrystal, shown in FIG. 21, displays the following peaks: $^1$H NMR (400 MHz, MeOD) δ: 0.87-0.94 (3H), 1.21-1.27 (3H), 1.28-1.39 (4H), 1.50-1.60 (2H), 1.64 (3H), 1.67 (3H), 1.70-1.78 (2H), 1.95-2.05 (1H), 2.15-2.25 (1H), 2.71-2.79 (2H), 2.79-2.89 (2H), 2.96-3.10 (1H), 3.92-4.04 (1H), 4.41-4.49 (2H), 5.20 (1H), 6.14 (1H), 6.39 (1H) and 7.96 (1H). The peak at 6.39 ppm in the 1H NMR spectrum corresponds to one proton of ethyl maltol. Comparison of the integration of this peak with that at 6.14 ppm, which corresponds to one of the aromatic protons of cannabidiolic acid, indicates that the cocrystal has an API: coformer stoichiometry of 1:1.

4.6 Infrared Spectrum of the 1:1 Cannabidiolic Acid Ethyl Maltol Cocrystal

Figure 22:
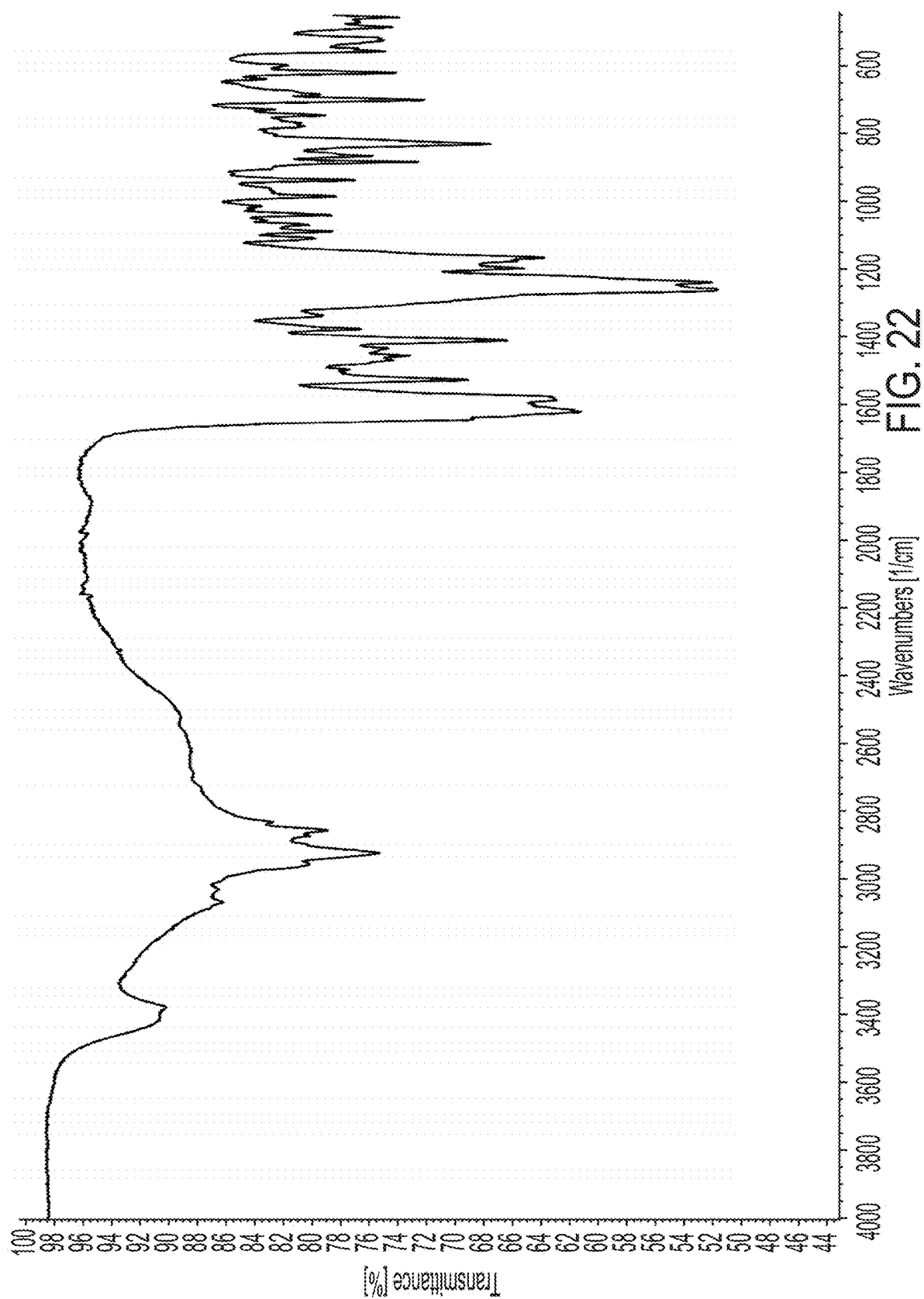
FIG. 22 depicts the infrared spectrum for the 1:1 cannabidiolic acid ethyl maltol cocrystal, according to an exemplary embodiment.

The experimental infrared Spectrum of the 1:1 cannabidiolic acid ethyl maltol cocrystal is shown in FIG. 22. The significant peaks identified in the experimental infrared spectrum of FIG. 22 are 3379, 3068, 3030, 2955, 2923, 2856, 2832, 1621, 1586, 1526, 1469, 1456, 1435, 1376, 1336, 1260, 1238, 1197, 1166, 1109, 1088, 1068, 1040, 986, 937, 884, 867, 831, 779, 746, 700, 683, 619, 556, 525, 484 and 456 cm$^{-1}$±1 cm$^{-1}$. The entire list of peaks, or a subset thereof, may be sufficient to characterize the cocrystal, as well as by an infrared pattern substantially similar to FIG. 22. For example, the 1:1 cannabidiolic acid ethyl maltol cocrystal may be characterized by at least three peaks selected from the peaks at 1526, 1410, 1376, 1260 and 1238 cm$^{-1}$±1 cm$^{-1}$.

Example 5: 1:1 Cannabidiolic acid L-Proline Cocrystal 5.1 Preparation of a 1:1 Cannabidiolic L-Proline Cocrystal The batch of the 1:1 cannabidiolic L-proline cocrystal used for characterisation was prepared as follows: Cannabidiolic acid (100 mg, 0.28 mmol) and L-proline (32 mg, 0.28 mmol) were weighed into a glass vial and nitromethane (1 ml) was added. The resulting slurry was placed in a shaker and matured for 48 hours (room temperature to 40° C. on an 8-hour cycle, heating to 40° C. for 4 hours and then cooling to RT for a further 4 hours). The product was then filtered under vacuum and dried under ambient conditions overnight.

5.2 XRPD Characterisation of a 1:1 Cannabidiolic Acid L-Proline Cocrystal

Figure 23:
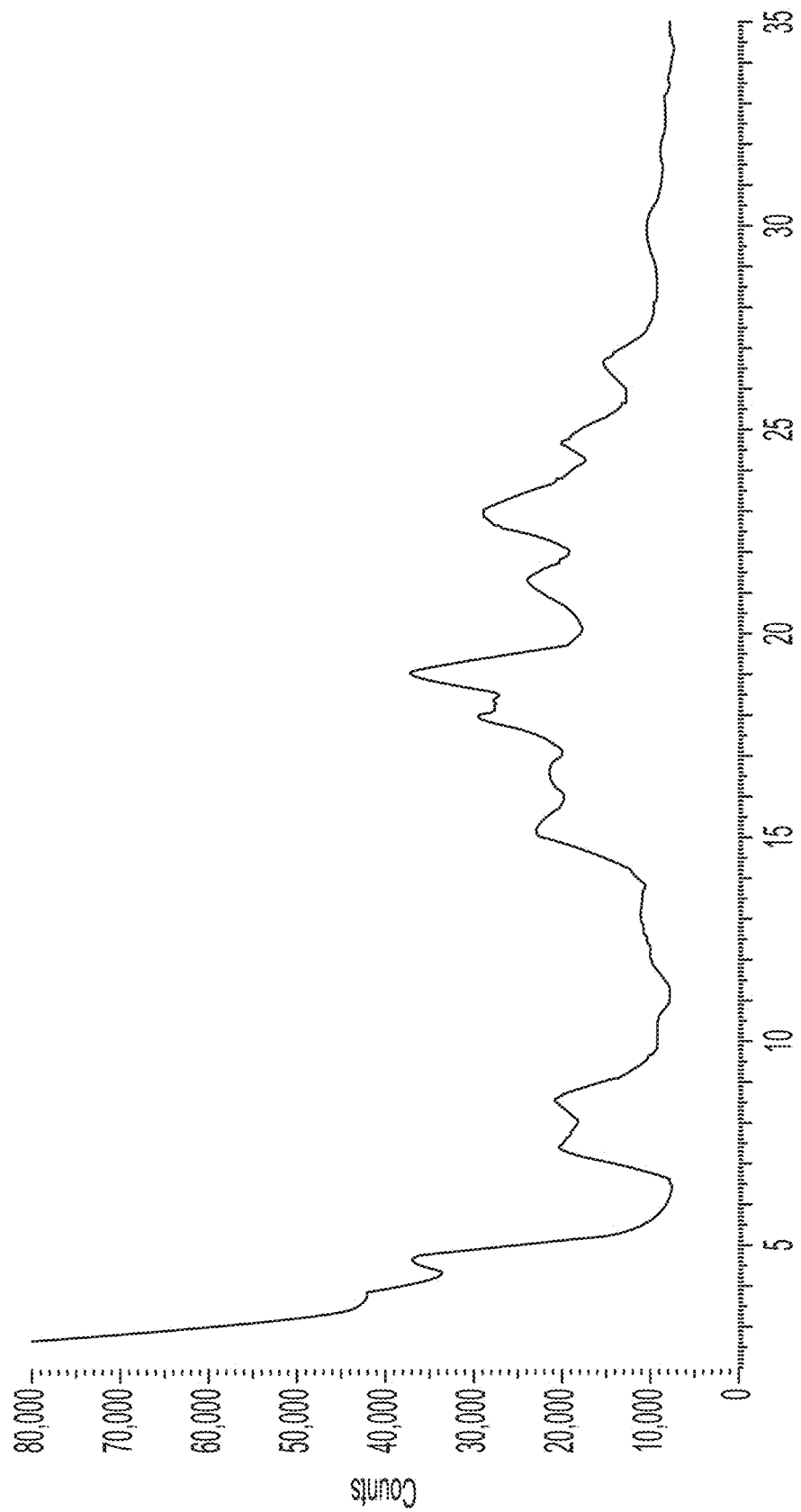
FIG. 23 depicts the XRPD diagram of the 1:1 cannabidiolic acid L-proline cocrystal, according to an exemplary embodiment.

The experimental XRPD pattern of the 1:1 cannabidiolic L-proline cocrystal is shown in FIG. 23. Table 5 lists the angles, °2θ±0.2 °2θ, and d-spacing of the peaks identified in the experimental XRPD pattern of FIG. 23. The entire list of peaks, or a subset thereof, may be sufficient to characterize the cocrystal, as well as by an XRPD pattern substantially similar to FIG. 23.

TABLE 6

| Angle °2θ ± 0.2 °2θ | d value Angstrom | Intensity % |
|---|---|---|
| 4.6 | 19.08 | 48% |
| 7.4 | 11.86 | 48% |
| 8.5 | 10.34 | 49% |
| 15.2 | 5.81 | 49% |
| 16.6 | 5.33 | 44% |
| 19.0 | 4.66 | 100% |
| 21.3 | 4.17 | 48% |
| 23.0 | 3.87 | 67% |
| 24.7 | 3.60 | 36% |
| 26.6 | 3.35 | 20% |

5.3 DSC of the 1:1 Cannabidiolic Acid L-Proline Cocrystal

Figure 24:
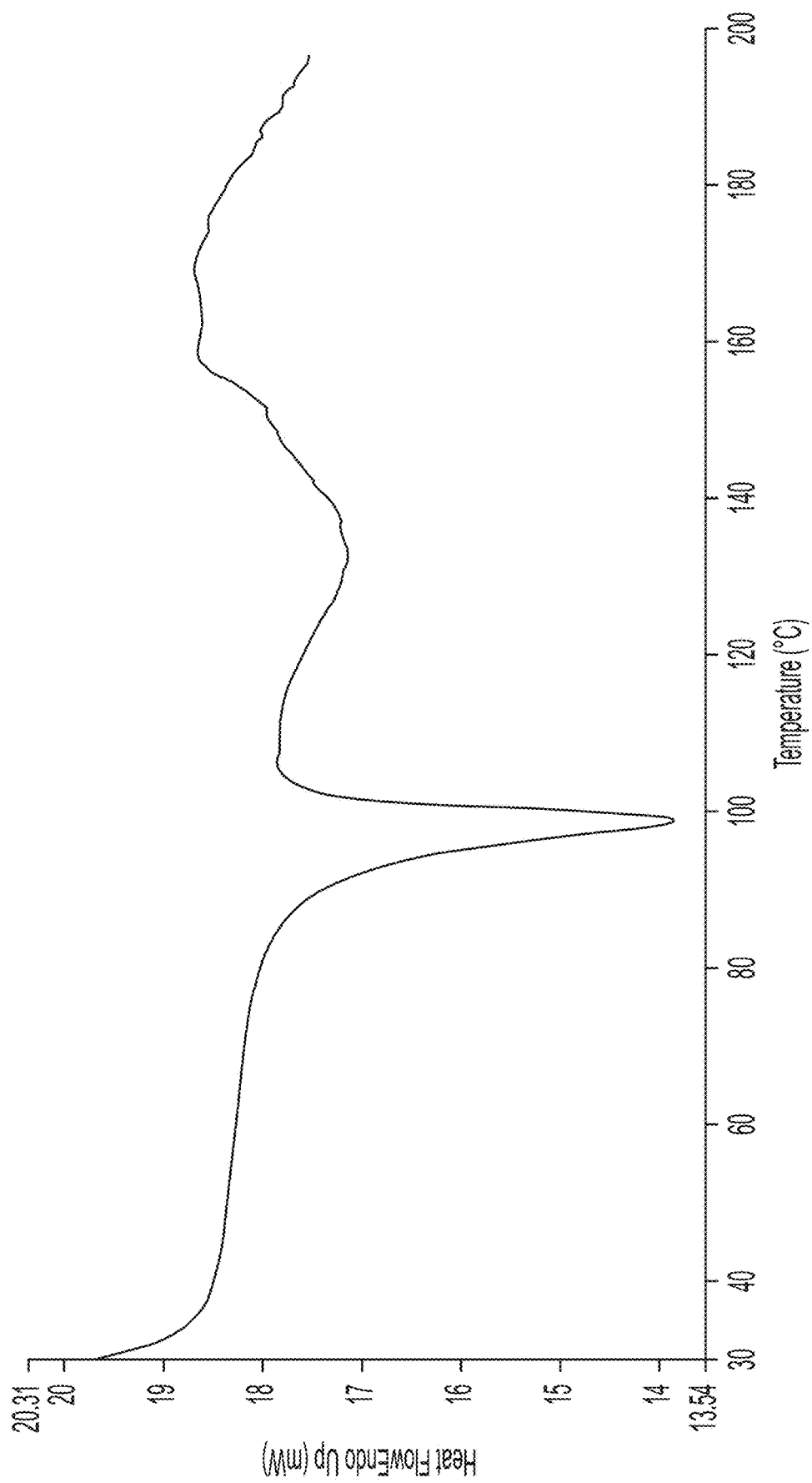
FIG. 24 depicts the DSC trace for the 1:1 cannabidiolic acid L-proline cocrystal, according to an exemplary embodiment.

The differential scanning calorimetry (DSC) trace, FIG. 24, shows a single endotherm with a peak maximum of 98.9° C.

5.4 TGA of the 1:1 Cannabidiolic Acid L-Proline Cocrystal

Figure 25:
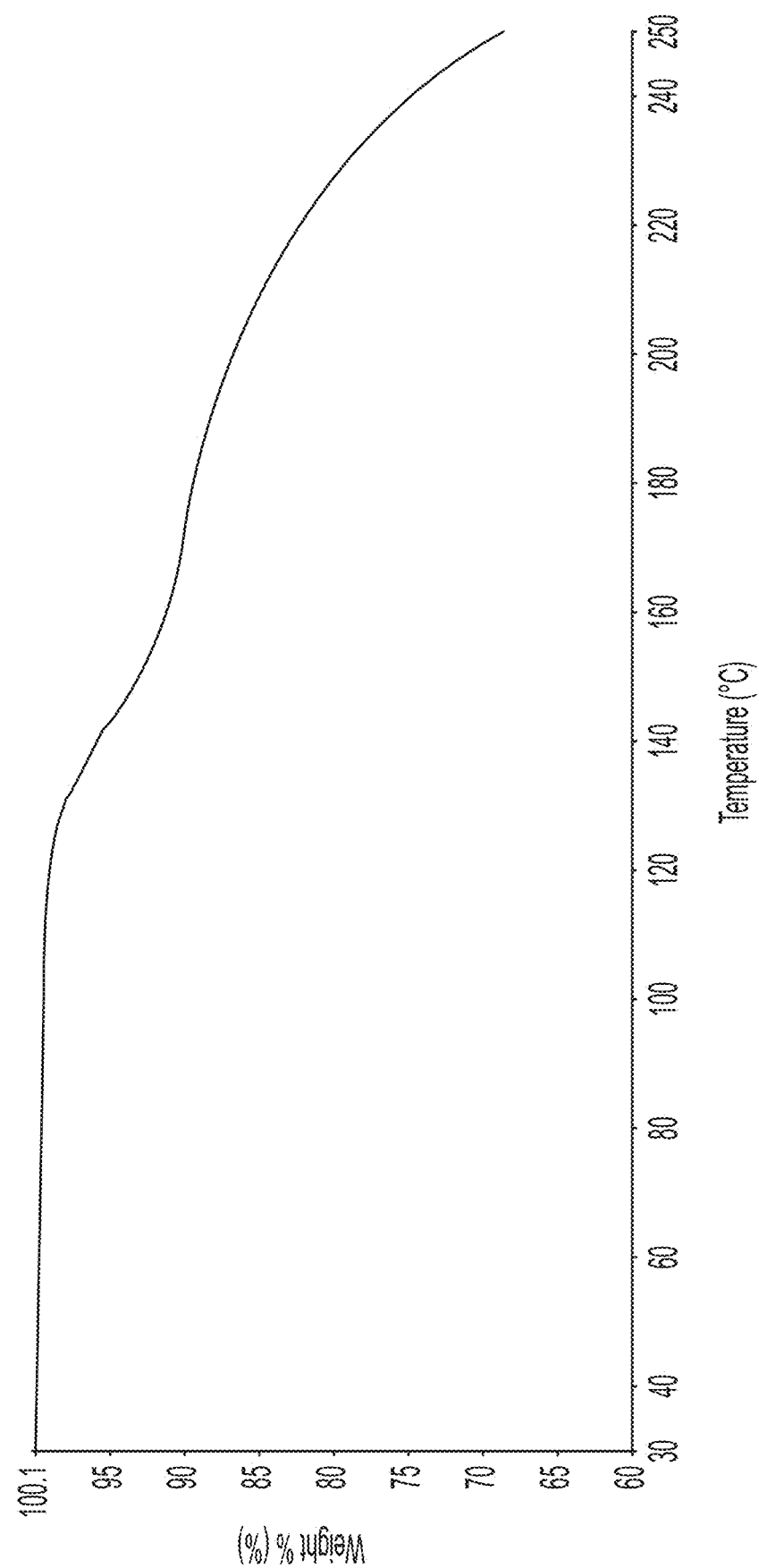
FIG. 25 depicts the TGA trace for the 1:1 cannabidiolic acid L-proline cocrystal, according to an exemplary embodiment.

The thermal gravimetric analysis (TGA) trace, FIG. 25, shows no significant weight loss prior to 110° C. A weight loss of approximately 10% can be seen over the temperature range 110-170° C. which is expected to be due to the decarboxylation of the CBDA following the melt of the cocrystal.

5.5 $^1$H NMR Spectrum of 1:1 Cannabidiolic Acid L-Proline Cocrystal

Figure 26:
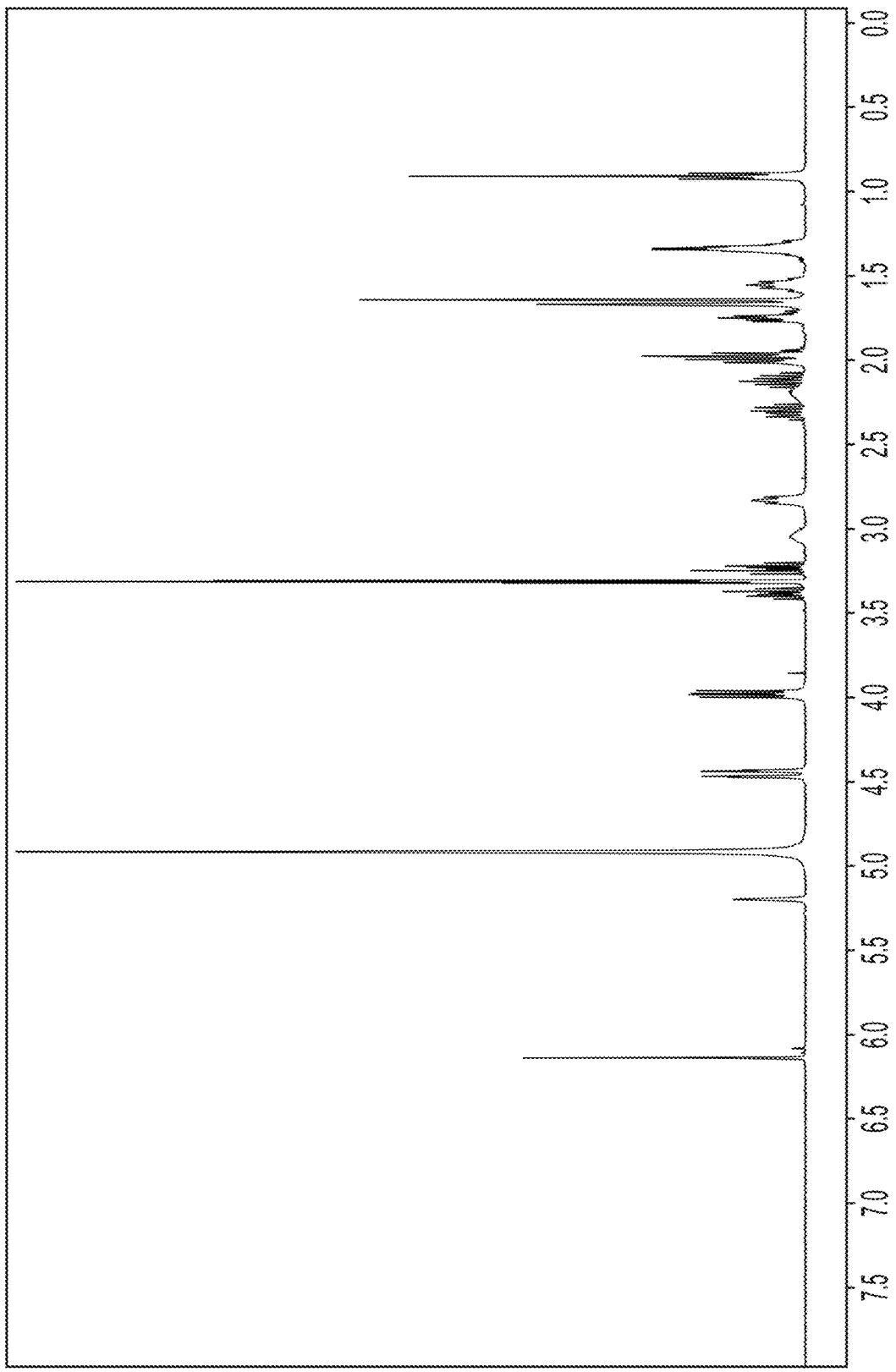
FIG. 26 depicts the 1H NMR spectrum for the 1:1 cannabidiolic acid L-proline cocrystal, according to an exemplary embodiment.

The $^1$H NMR spectrum of the 1:1 cannabidiolic acid L-proline cocrystal, shown in FIG. 26, displays the following peaks: $^1$H NMR (400 MHz, MeOD) δ: 0.88-0.93 (3H), 1.28-1.38 (4H), 1.51-1.59 (2H), 1.64 (3H), 1.66 (3H) 1.70-1.78 (2H), 1.94-2.04 (3H), 2.06-2.24 (2H), 2.25-2.36 (1H), 2.78-2.88 (2H), 2.96-3.11 (1H), 3.18-3.28 (1H), 3.34-3.42 (1H), 3.95-4.03 (2H), 4.40-4.50 (2H), 5.20 (1H) and 6.13 (1H). The peak at 3.33-3.42 ppm in the 1H NMR spectrum corresponds to one proton of L-proline. Comparison of the integration of this peak with that at 6.13 ppm, which corresponds to one of the aromatic protons of cannabidiolic acid, indicates that the cocrystal has an API: coformer stoichiometry of 1:1.

5.6 Infrared Spectrum of the 1:1 Cannabidiolic Acid L-Proline Cocrystal

Figure 27:
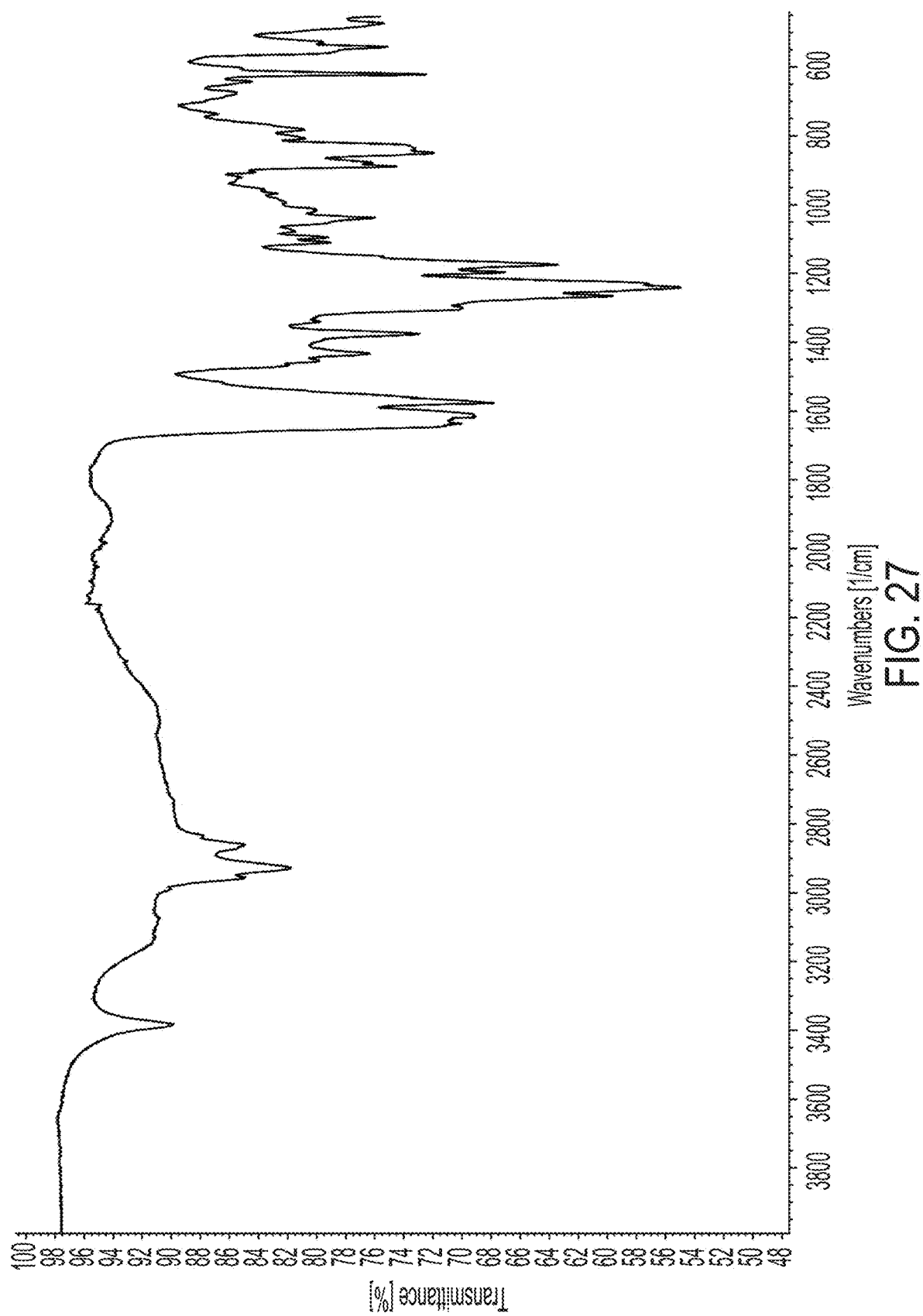
FIG. 27 depicts the infrared spectrum for the 1:1 cannabidiolic acid L-proline cocrystal, according to an exemplary embodiment.

The experimental infrared Spectrum of the 1:1 cannabidiolic acid L-proline cocrystal is shown in FIG. 27. The significant peaks identified in the experimental infrared spectrum of FIG. 27 are 3384, 2955, 2926, 2859, 1614, 1574, 1430, 1374, 1338, 1262, 1240, 1194, 1172, 1108, 1092, 1036, 885, 846, 803, 778, 733, 673, 640, 618, 539 and 471 cm$^{-1}$±1 cm$^{-1}$. The entire list of peaks, or a subset thereof, may be sufficient to characterize the cocrystal, as well as by an infrared pattern substantially similar to FIG. 27. For example, the 1:1 cannabidiolic acid L-proline cocrystal may be characterized by at least three peaks selected from the peaks at 1574, 1430, 1374, 1240 and 1172 cm$^{-1}$±1 cm$^{-1}$.

Example 6: 1:1 Cannabidiolic Acid D-Proline Cocrystal 6.1 Preparation of a 1:1 Cannabidiolic D-Proline Cocrystal The batch of the 1:1 cannabidiolic D-proline cocrystal used for characterisation was prepared as follows: Cannabidiolic acid (56 mg, 0.16 mmol) and L-proline (18 mg, 0.16 mmol) were weighed into a glass vial and nitromethane (1 ml) was added. The resulting slurry was placed in a shaker and matured for 48 hours (room temperature to 40° C. on an 8-hour cycle, heating to 40° C. for 4 hours and then cooling to RT for a further 4 hours). The product was then filtered under vacuum and dried under ambient conditions overnight.

6.2 XRPD Characterisation of a 1:1 Cannabidiolic Acid D-Proline Cocrystal

Figure 28:
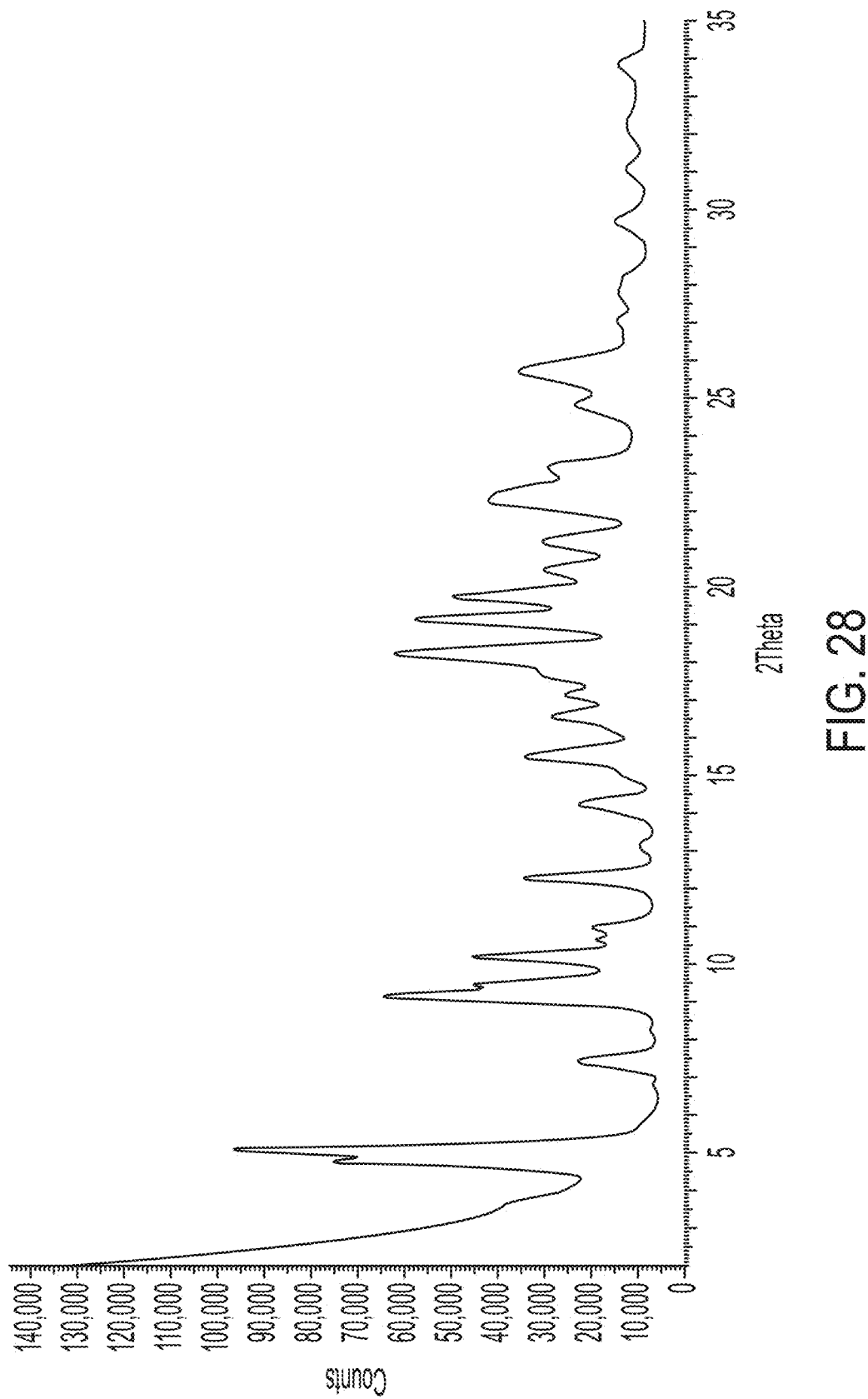
FIG. 28 depicts the XRPD diagram of the 1:1 cannabidiolic acid D-proline cocrystal, according to an exemplary embodiment.

The experimental XRPD pattern of the 1:1 cannabidiolic D-proline cocrystal is shown in FIG. 28. Table 6 lists the angles, °2θ±0.2 °2θ, and d-spacing of the peaks identified in the experimental XRPD pattern of FIG. 28. The entire list of peaks, or a subset thereof, may be sufficient to characterize the cocrystal, as well as by an XRPD pattern substantially similar to FIG. 28.

TABLE 6

| Angle °2θ ± 0.2 °2θ | d value Angstrom | Intensity % |
|---|---|---|
| 4.8 | 18.57 | 67% |
| 5.1 | 17.43 | 100% |
| 7.4 | 11.91 | 21% |
| 9.1 | 9.68 | 77% |
| 9.4 | 9.36 | 51% |
| 10.2 | 8.69 | 52% |
| 10.6 | 8.32 | 15% |
| 11.0 | 8.07 | 17% |
| 12.3 | 7.21 | 38% |
| 14.2 | 6.22 | 20% |
| 15.5 | 5.72 | 37% |
| 16.5 | 5.36 | 28% |
| 17.1 | 5.18 | 24% |
| 18.2 | 4.87 | 80% |
| 19.1 | 4.64 | 73% |
| 19.7 | 4.50 | 60% |
| 20.4 | 4.35 | 31% |
| 21.2 | 4.19 | 31% |
| 22.3 | 3.98 | 49% |
| 23.2 | 3.83 | 28% |
| 24.8 | 3.59 | 21% |
| 25.7 | 3.47 | 39% |
| 27.0 | 3.30 | 8% |
| 27.8 | 3.21 | 8% |
| 29.7 | 3.01 | 10% |

6.3 DSC of the 1:1 Cannabidiolic Acid D-Proline Cocrystal

Figure 29:
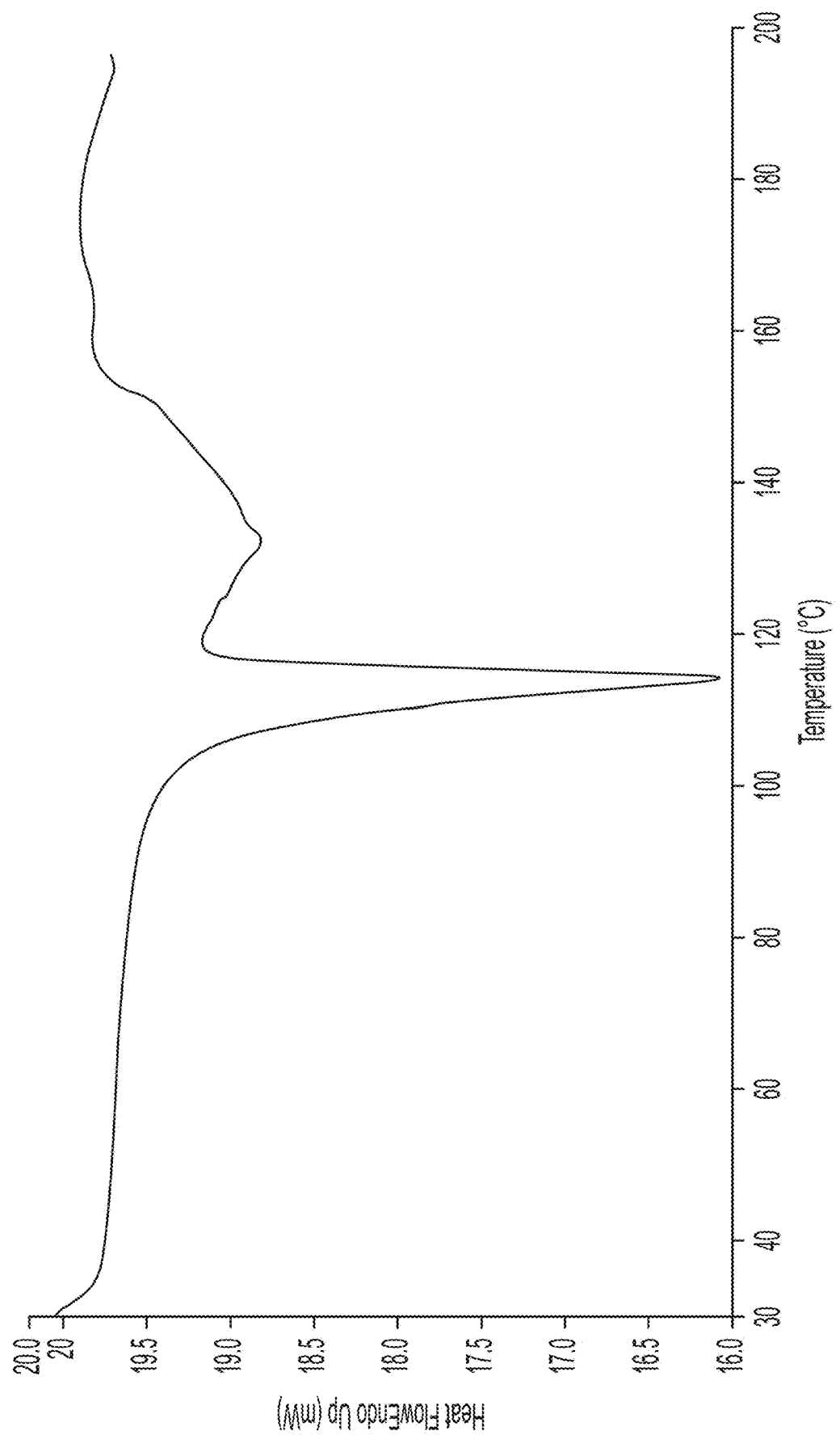
FIG. 29 depicts the DSC trace for the 1:1 cannabidiolic acid D-proline cocrystal, according to an exemplary embodiment.

The differential scanning calorimetry (DSC) trace, FIG. 29, shows a single endotherm with a peak maximum of 114° C.

6.4 TGA of the 1:1 Cannabidiolic Acid D-Proline Cocrystal

Figure 30:
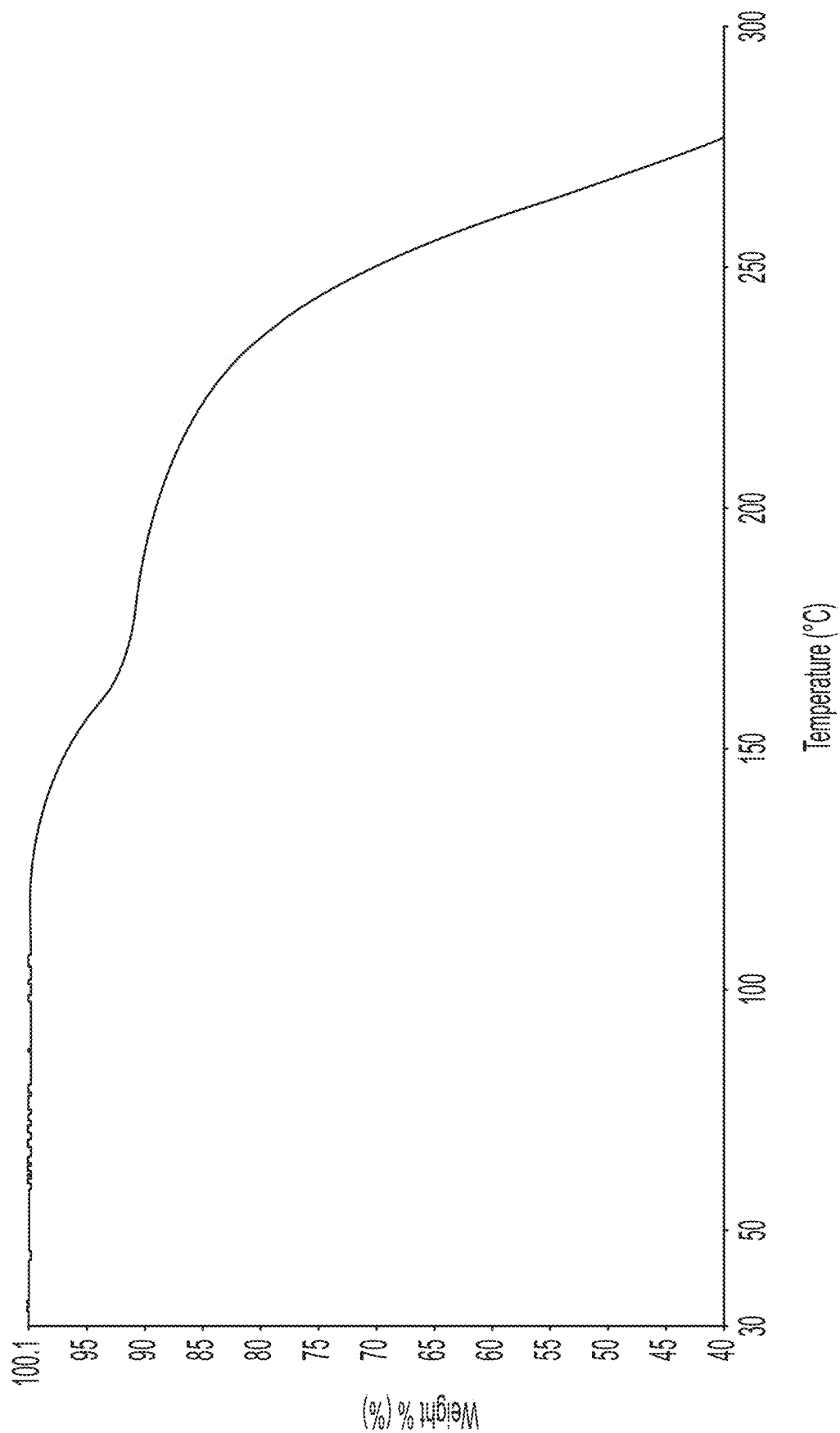
FIG. 30 depicts the TGA trace for the 1:1 cannabidiolic acid D-proline cocrystal, according to an exemplary embodiment.

The thermal gravimetric analysis (TGA) trace, FIG. 30, shows no significant weight loss prior to 115° C. A weight loss of approximately 10% can be seen over the temperature range 115-170° C. which is expected to be due to the decarboxylation of the CBDA following the melt of the cocrystal.

6.5 $^1$H NMR Spectrum of 1:1 Cannabidiolic Acid D-Proline Cocrystal

Figure 31:
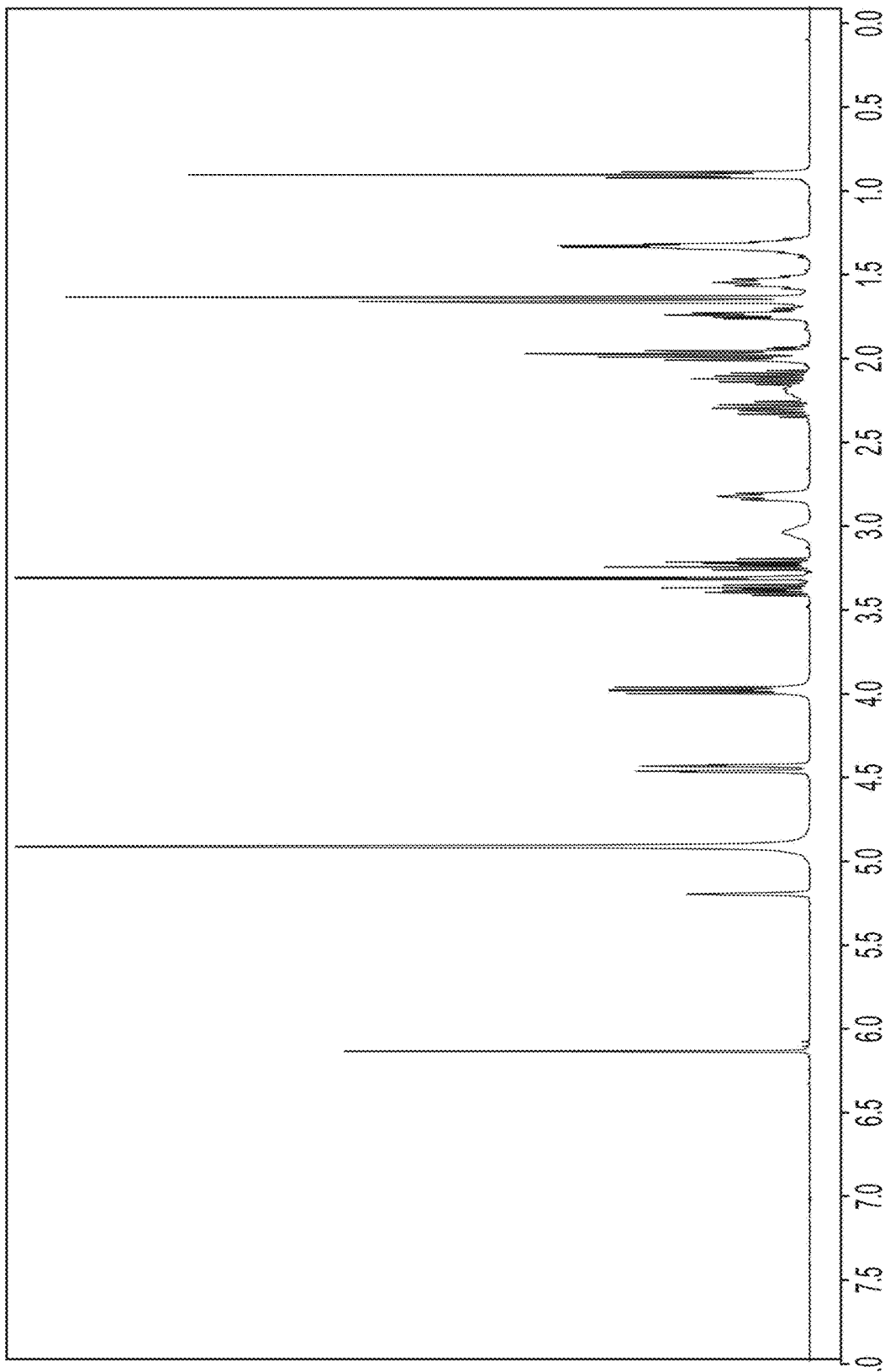
FIG. 31 depicts the 1H NMR spectrum for the 1:1 cannabidiolic acid D-proline cocrystal, according to an exemplary embodiment.

The $^1$H NMR spectrum of the 1:1 cannabidiolic acid D-proline cocrystal, shown in FIG. 31, displays the following peaks: $^1$H NMR (400 MHz, MeOD) δ: 0.88-0.93 (3H), 1.28-1.38 (4H), 1.50-1.60 (2H), 1.64 (3H), 1.66 (3H), 1.70-1.80 (2H), 1.94-2.04 (3H), 2.07-2.24 (2H), 2.25-2.36 (1H), 2.78-2.88 (2H), 2.95-3.12 (1H), 3.18-3.28 (1H), 3.33-3.44 (1H), 3.94-4.03 (2H), 4.40-4.50 (2H), 5.20 (1H) and 6.13 (1H). The peak at 3.33-3.44 ppm in the 1H NMR spectrum corresponds to one proton of D-proline. Comparison of the integration of this peak with that at 6.13 ppm, which corresponds to one of the aromatic protons of cannabidiolic acid, indicates that the cocrystal has an API: coformer stoichiometry of 1:1.

6.6 Infrared Spectrum of the 1:1 Cannabidiolic Acid D-Proline Cocrystal

Figure 32:
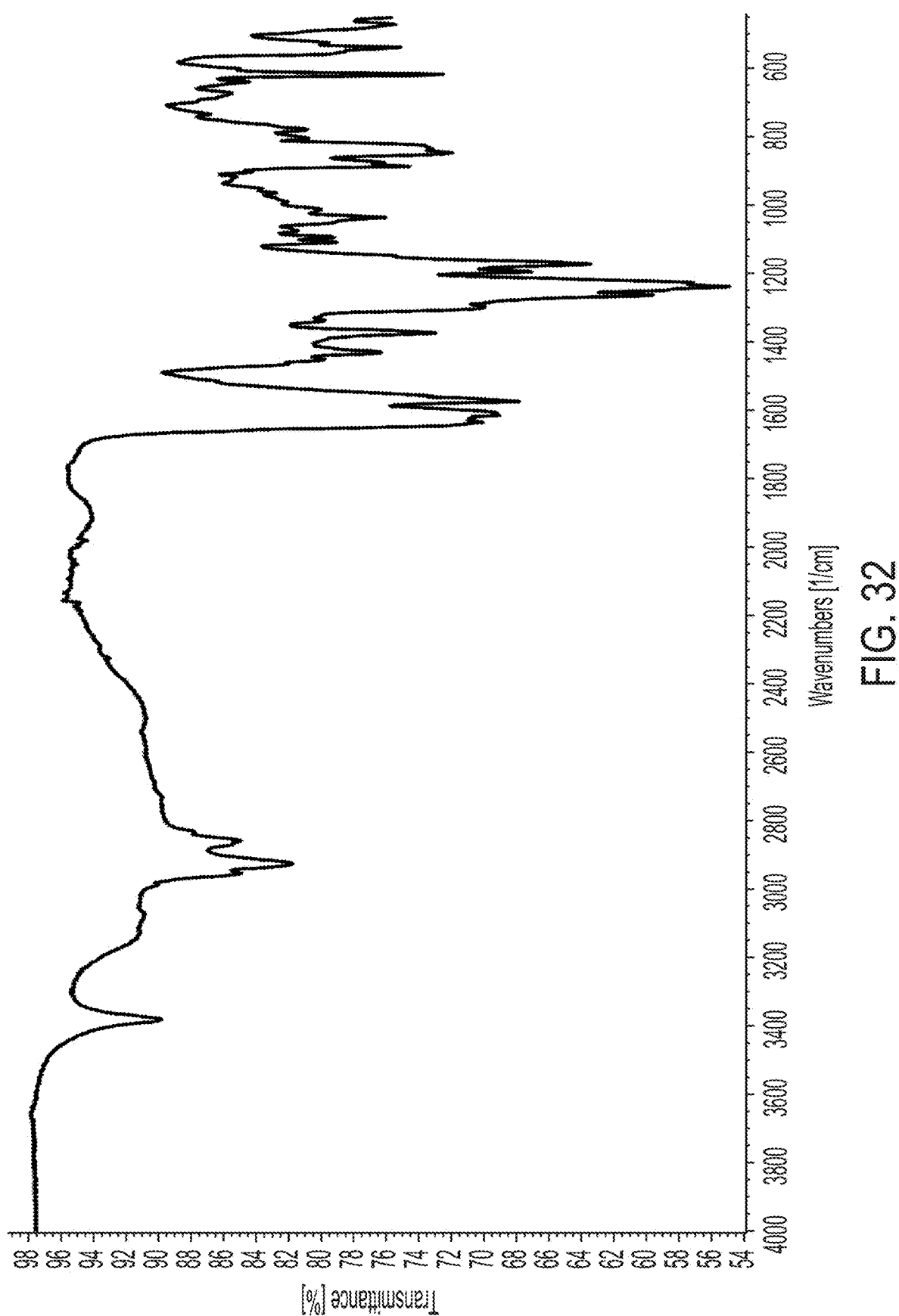
FIG. 32 depicts the infrared spectrum for the 1:1 cannabidiolic acid D-proline cocrystal, according to an exemplary embodiment.

The experimental infrared spectrum of the 1:1 cannabidiolic acid D-proline cocrystal is shown in FIG. 32. The significant peaks identified in the experimental infrared spectrum of FIG. 32 are 3409, 3384, 3360, 2925, 2858, 1635, 1611, 1575, 1454, 1429, 1374, 1306, 1261, 1244, 1223, 1191, 1111, 1094, 1079, 1051, 1036, 1011, 994, 964, 929, 884, 873, 846, 819, 774, 731, 675, 646, 617, 589, 556, 538, 490, 466 and 452 cm$^{-1}$±1 cm$^{-1}$. The entire list of peaks, or a subset thereof, may be sufficient to characterize the cocrystal, as well as by an infrared pattern substantially similar to FIG. 32. For example, the 1:1 cannabidiolic acid D-proline cocrystal may be characterized by at least three peaks selected from the peaks at 1635, 1611, 1575, 1374 and 1244 cm$^{-1}$±1 cm$^{-1}$.

Example 7: Solid-State Stability Study for the Cannabidiolic Acid Cocrystals

The physical stability of the cannabidiolic acid cocrystals was examined with respect to solid form conversion or signs of decomposition or decarboxylation, and to compare the results with those for pure cannabidiolic acid. In order to assess the storage potential of the cocrystals within a reasonable timeframe standard accelerated storage conditions of 40° C. and 75% relative humidity were chosen. 50 mg each of the 1:1 cannabidiolic acid L-phenylalanine, 1:1 cannabidiolic acid vanillin, 1:1 cannabidiolic acid betaine, 1:1 cannabidiolic acid ethyl maltol, 1:1 cannabidiolic acid L-proline and cannabidiolic acid were separately placed in a sealed container at 40° C. and 75% relative humidity and monitored periodically over a 4-week time period. The results of the study are shown in Table 7. All samples that had not decomposed and remained as solids were analyzed by XRPD after this time to observe any potential form changes. At the start of the study, all cocrystal samples were white solids while the pure cannabidiolic acid was an off-white solid.

TABLE 7

| | 40° C./75% RH | | |
|---|---|---|---|
| CBDA Form | Time | Appearance | XRPD |
| Pure CBDA | 2 hours | Dark brown liquid | N/A |
| 1:1 CBDA Phenylalanine Cocrystal | 4 weeks | No change | No change (as FIG. 2) |
| 1:1 CBDA Vanillin Cocrystal | 3 weeks | Dark brown liquid | N/A |
| 1:1 CBDA Betaine Cocrystal | 4 weeks | No change | No change (as FIG. 12) |
| 1:1 CBDA Ethyl Maltol Cocrystal | 2 weeks | Dark brown liquid | N/A |
| 1:1 CBDA L-Proline Cocrystal | 4 weeks | tan solid | No change (as FIG. 22) |

Within one hour of the study commencing the pure CBDA had deliquesced to produce a liquid that within a further hour had turned dark brown in color indicating rapid decomposition under these storage conditions. The 1:1 cannabidiolic acid ethyl maltol and 1:1 cannabidiolic acid vanillin cocrystals had also converted into dark brown liquids within 2 and 3 weeks respectively, indicating that while they are more stable than pure cannabidiolic acid under these storage conditions they also begin to decompose over a short period of time. After four weeks the 1:1 cannabidiolic acid L-proline cocrystal, while still possessing the same crystalline structure by XRPD, had begun to change color becoming a tanned colored solid. However, the 1:1 cannabidiolic acid L-phenylalanine and 1:1 cannabidiolic acid betaine cocrystals remained unchanged as white solids and XRPD analysis confirmed that no solid form conversion or dissociation had occurred showing that they these cocrystals are stable to storage under these conditions. The results of this study suggest that the 1:1 cannabidiolic acid L-phenylalanine and 1:1 cannabidiolic acid betaine cocrystals have significantly superior storage properties compared to pure CBDA and that they do not dissociate, decompose or decarboxylate under accelerated conditions. The study also shows that the 1:1 cannabidiolic acid L-phenylalanine and 1:1 cannabidiolic acid betaine cocrystals have superior storage properties compared to the other cocrystals of this invention.

What is claimed is:

1. A composition comprising: a cannabidiolic acid cocrystal, wherein the cannabidiolic acid cocrystal is selected from the group consisting of: a 1:1 cannabidiolic acid L-phenylalanine cocrystal, a 1:1 cannabidiolic acid vanillin cocrystal, a 1:1 cannabidiolic acid betaine cocrystal, a 1:1 cannabidiolic acid ethyl maltol cocrystal, a 1:1 cannabidiolic acid L-proline cocrystal, and a 1:1 cannabidiolic acid D-proline cocrystal.

2. The composition of claim 1, wherein the cannabidiolic acid L-phenylalanine cocrystal is characterized by:
   a powder X-ray diffraction pattern having at least three peaks selected from 3.1, 6.4, 18.4, 19.8, and 23.7 °2θ±0.2 °2θ; or
   a powder X-ray diffraction pattern substantially similar to FIG. 3; or
   an infrared spectrum having at least three peaks selected from 1606, 1409, 1296, 1240 and 1184 $cm^{-1}\pm 1$ $cm^{-1}$; or
   an infrared spectrum substantially similar to FIG. 7.

3. The composition of claim 1, wherein the cannabidiolic acid vanillin cocrystal is characterized by:
   a powder X-ray diffraction pattern having at least three peaks selected from 4.3, 7.5, 14.2, 19.4, 22.2, and 25.2 °2θ±0.2 °2θ; or
   a powder X-ray diffraction pattern substantially similar to FIG. 8; or
   an infrared spectrum having at least three peaks selected from 1658, 1509, 1294, 1258 and 1151 $cm^{-1}\pm 1$ $cm^{-1}$; or
   an infrared spectrum substantially similar to FIG. 12.

4. The composition of claim 1, wherein the cannabidiolic acid betaine cocrystal is characterized by:
   a powder X-ray diffraction pattern having at least three peaks selected from 7.2, 11.0, 16.3, 18.4, and 23.6 °2θ±0.2 °2θ; or
   a powder X-ray diffraction pattern substantially similar to FIG. 13; or
   an infrared spectrum having at least three peaks selected from 1723, 1589, 1371, 1261 and 887 $cm^{-1}\pm 1$ $cm^{-1}$; or
   an Infrared Spectrum substantially similar to FIG. 17.

5. The composition of claim 1, wherein the cannabidiolic acid ethyl maltol cocrystal is characterized by:
   a powder X-ray diffraction pattern having at least three peaks selected from 8.4, 16.0, 17.1, 18.0, and 19.7 °2θ±0.2 °2θ; or
   a powder X-ray diffraction pattern substantially similar to FIG. 18; or
   an infrared spectrum having at least three peaks selected from 1526, 1410, 1376, 1260 and 1238 $cm^{-1}\pm 1$ $cm^{-1}$; or
   an infrared spectrum substantially similar to FIG. 22.

6. The composition of claim 1, wherein the cannabidiolic acid L-proline cocrystal is characterized by:
   a powder X-ray diffraction pattern having at least three peaks selected from 7.4, 8.5, 15.2, 19.0, and 23.0 °2θ±0.2 °2θ; or
   a powder X-ray diffraction pattern substantially similar to FIG. 23; or
   an infrared spectrum having at least three peaks selected from 1574, 1430, 1374, 1240 and 1172 $cm^{-1}\pm 1$ $cm^{-1}$; or
   an infrared spectrum substantially similar to FIG. 27.

7. The composition of claim 1, wherein the cannabidiolic acid D-proline cocrystal is characterized by:
   a powder X-ray diffraction pattern having at least three peaks selected from 4.8, 5.1, 9.1, 18.2, and 19.1 °2θ±0.2 °2θ; or
   a powder X-ray diffraction pattern substantially similar to FIG. 28; or
   an Infrared Spectrum having at least three peaks selected from 1635, 1611, 1575, 1374 and 1244 $cm^{-1}\pm 1$ $cm^{-1}$; or
   an infrared spectrum substantially similar to FIG. 32.

8. The composition comprising: the cannabidiolic acid cocrystal of claim 1 and an excipient.

* * * * *